(12) United States Patent
Utt et al.

(10) Patent No.: US 6,482,924 B1
(45) Date of Patent: Nov. 19, 2002

(54) LEPTOSPIRA VACCINE ANTIGENS FOR THE PREVENTION OF LEPTOSPIROSIS

(75) Inventors: Eric A. Utt, Groton, CT (US); Michael Stephen Willy, North Stonington, CT (US); Don A. Dearwester, Westerly, RI (US)

(73) Assignees: Pfizer Inc., New York, NY (US); Pfizer Products, Inc., Groton, CT (US)

(*) Notice: Subject to any disclaimer, the term of this patent is extended or adjusted under 35 U.S.C. 154(b) by 0 days.

(21) Appl. No.: 09/461,920

(22) Filed: Dec. 15, 1999

Related U.S. Application Data
(60) Provisional application No. 60/113,288, filed on Dec. 22, 1998.

(51) Int. Cl.[7] .................. C07K 1/00; A61K 39/09; A61K 39/00; A61K 39/02; A61K 38/00
(52) U.S. Cl. ............... 530/350; 530/806; 530/825; 424/234.1; 424/184.1; 424/190.1; 514/2
(58) Field of Search ................ 530/350, 825, 530/820, 806; 424/234.1, 184.1, 190.1; 514/2

(56) References Cited

PUBLICATIONS

Farr, R. W.; Leptospirosis; Clin. Infect. Dis.; 21: 1–8 (1995).
Miller, D.A., et al.; Survey to estimate prevalence of Leptospira interrogans infection in mature cattle in the United States; Am. J. Vet. Res.; vol. 52, No. 11: 1761–1765 (1991).
Stamper, M.A., et al.; Leptospirosis in Rehabilitated Pacific Harbor Seals from California; J. Wild. Dis.; 34(2): 407–410 (1989).
Vinetz, J.M.; Leptospirosis; Cur. Opin. Infect. Dis.; 10: 357–361 (1997).
Baranton, G.; The Spirochaetes: a different way of life; Bull. Inst. Pasteur; 93: 63–95 (1995).
Thiermann, A.B., et al.; Leptospirosis: Current developments and trends; J. Am. Vet. Med. Assoc.; 184: 722–725 (1984).
Wallace, et al.; The use of synthetic oligonucleotides as hybridization probes; Nucleic Acid Research; 9: 879–894 (1981).
Thanh v. Huynh, et al.; Constructing and Screening cDNA Libraries in λgt10 and λgt11; A Practical Approach; 1: 49–78 (1985).
Glyllenstein, et al.; Generation of Single–stranded DNA by the polymerase chain reaction and its application to direct sequencing of HLA–DQA locus; Proc. Nat'l Acad. Sci.; 85: 7652–7656 (1988).
Ochman, et al.; Genetic Applications of an Inverse Polymerase Chain Reaction; Genetics; 120: 621–623 (1988).
Behnaz Taidi–Laskowski, et al.; Use of RecA protein to enrich for homologous genes in a genomic library; Nucleic Acids Research; vol. 16 No. 16, 8156–8169 (1988).

Frohman, et al.; Rapid production of full–length cDNAs from rare transcripts; Proc. Nat'l Acad. Sci.; 85: 8998–9002 (1988).
Loh, et al.; Polmerase Chain Reaction with Single–Sided Specificity: Analysis of T Cell receptor δ Chain; Science; 243: 217–220 (1989).
Ausubel, et al.; Current Protocols in Molecular Biology; vol. 2, ed. Green Publish. Assoc. & Wiley Interscience; Ch. 13 (1988).
Grant, et al.; Expression and Secretion Vectors for Yeast; Methods in Enzymology; vol. 153: 516–544 (1987).
Rothstein; Cloning in Yeast; vol. II. IRL Press; Chapter 3, pp. 45–66 (1988).
Bitter; Heterologous Gene Expression in Yeast; Methods in Enzymology, vol. 152, pp 673–684 (1987).
Logan, et al.; Adenovirus tripartite leader sequence enhances translation of mRNAs late after infection; Proc. Natl. Acad. Sci.; 81: 3655–3659 (1984).
Mackett, et al.; Vaccinia virus: A selectable eukaryotic cloning and expression vector; Proc. Natl. Acad. Sci.; 79: 7415–7419 (1982).
Mackett, et al.; General Method for Production and Selection of Infectious Vaccinia Virus Recombinants Expressing Foreign Genes; J. of Virol. 49: 857–864 (1984).
Panicali, et al.; Construction of poxviruses as cloning vectors: Proc. Natl. Acad. Sci.; vol. 79 pp 4927–4931 (1982).
Goedert, et al.; Cloning and sequencing of the cNDA encoding a core protein of the paired helical filament of Alzheimer disease; Proc. Natl. Acad. Sci.; 85: 4051–4055 (1988).
Heinemann, et al.; Bacterial conjugative plasmids mobilize DNA transfer between bacteria and yeast; Nature; 340: 205–209 (1989).
Bitter, et al.; Expression and Secretion Vectors for Yeast; Methods in Enzymology; vol. 153, pp 516–544 (1987).
Rose, et al.; A *Saccharomyces cerevisiae* genomic plamid bank on a centromere–containing shuttle vector; Gene; 60: 237–243 (1987).
Kohler, et al., Nature; 256: 495–497 (1975).
Merrifield; Solid Phase Synthesis; Science; 242: 341–347 (1986).
Tam, et al.; $S_N2$ Deprotection of Synthetic Peptides with a Low Concentration of HF in Dimethyl Sulfide; J. Am. Chem. Soc.; 105: 6442–6455 (1983).
Diener, et al.; Specific Immunosuppression by Immunotoxins Containing Daunomycin; Science; 231: 148–150 (1986).

*Primary Examiner*—S. Devi
(74) *Attorney, Agent, or Firm*—Paul H. Ginsburg; Lorraine B. Ling; Kohn & Associates

(57) ABSTRACT

Four antigenic preparations are provided, each of which contains a different protein from Leptospira which can be used immunologically in vaccines for leptospirosis caused by this organism. Also provided in the invention are polynucleotides encoding these four proteins and antibodies which bind the proteins for use in the diagnosis of leptospirosis.

2 Claims, 2 Drawing Sheets

FIGURE 1A)

ATATGCGATCCGTTCAAGAAAAGAACGAATTGATACAAGAAATTCATCATAGAGTTAGAAATAATCTT
CAGGTAATTTCCGGTTTAGTGGAAATGCATAGTGGGTCTGGTAAAGAGAATCTGCAAATCATATTATC
CGATTTTCAAAATCGTATATTAGCAATATCTGAAGTTCATAATTATTTATATAAGTCCGAAAATTATTTC
GAAATCGATTTTGTCGAGGTGATGGATAAGATTATTCTAAATCTTTCTTATAGATTGGGAAAACGTTC
GATCAAGATAGAAACTGAAGCTGAGTCTACTTTTTTAAGAATCGAAAATGCGATTCCTTGTGCTATGA
TTTTCAACGAATTGTTATCCAATTCTTTAAAACACGCTTTTCGTTCGGAAAAAGGAACCGTTCAAATTT
CGTTTCGAAAAAAAGGAGATAAATATTACCTTCAAGTTTCTGACAATGGTTCAGGAATCAAGGATTTT
AAAATTTGGTCCAAACCGAAAACGGCTGGTTTCACTTTGATACAAATATTAACAAAACAGATTAAAGG
TCGTTTTCAAATTTTCTCTGAAGGCGGTTTTACTGCGGTTTTAGAGTTCAACTCAATCTAAAAAAGGC
TAAATAAGTTATAGGTT

FIGURE 1B)

MRSVQEKNELIQEIHHRVRNNLQVISGLVEMHSGSGKENLQIILSDFQNRILAISEVHNYLYKSENYFEIDF
VEVMDKIILNLSYRLGKRSIKIETEAESTFLRIENAIPCAMIFNELLSNSLKHAFRSEKGTVQISFRKKGDKYY
LQVSDNGSGIKDFKIWSKPKTAGFTLIQILTKQIKGRFQIFSEGGFTAVLEFNSI.

FIGURE 2A)

ATGAAATTTTCAGGATTAACCAATCATATTTATAAAGACAGGGATTATCTTACTCGAAATAGGGCGTT
CCATCTTTTCATTTTTAATGTGGTGTCGCTTTTATTGGGTTTATCTGTGAATTTTTATGTTTGGTTTGTG
AAAGGTGATCTATTACGTCCTGGTTTTTTAATCATCATGCTTGCATCTGCAGTCTCTCTGTTTTTTTTA
TTGAGAAAAAAATTTGAATTGGCTCTCAGAATTATTTTGATCGCAAGTGTAATTGCTGTTAGCGTTGG
TTGGTTTTTTGGACTTTCTCAGGGAAATTCTCCTTTGGACGAAGGGAATAAAAATATTGTTTTAGCTAT
ATTTATTATGATTTTCTTATATTTTGCAAATGTAAAGCGAACTCTTCTAATTGCGGTTTACTGTTTTGTT
TTGATTTTTATGGAAGAGCTTTTAATGCAACAAATTCATGAATCTATTCACATGGCTGATCGAATCGCT
CTATTTTTCATGTTTTCTGTAATTTCGATTATCGCCGTAAGAACTCTTCATGGATCGATTGAAGAAAAG
AACGAATTGATACAAGAAATTCATCATAGAGTTAGAAATAATCTTCAGGTTCTTTCCGGTTTAGTAGAA
ATGCATAGTGATTCTGATCAAGGGAATCTTAGGAATATATTATCTGATTTTCAAAATCGTATATTAGCA
ATATCTGAAGTTCATAATTATTTATATAAGTCCGAAAATATTCGACATAGATTTTTCAGAAGTGATTG
AAAGAATCATTGCAAATCTCATTCATAAATTTGGTAAACAATCTGTAAAAATAGAAAATTTAACGGAAC
AGATTTTTTTAAGAATCGAATATGCGATTCCTTGTGCTATGATTTTTAGTGAACTTTTATCTAATTCTTT
AAAACATGCGTTTTCTTCGGATATGGGGAAAATTGTCATTCGGTTTCATAAAGAAGGAAATAAGTATC
GTCTTCAAATTGAAGATAATGGTTCTGGAATATCTGATTCTAAAACTTGGTTGAAACCAAAAACTTCTG
GTTTTAAATTGATTCAACTTTTGACCAGACAAATAAAAGGTGATTTTCAAATTCTTTCGGATTCTGGTT
CCATTGCTGTACTTGAATTTTACACTTAAGCATATTCAAAATTTAGAATATTAATTTAAA

FIGURE 2B)

MKFSGLTNHIYKDRDYLTRNRAFHLFIFNVVSLLLGLSVNFYVWFVKGDLLRPGFLIIMLASAVSLFFLLRK
KFELALRIILIASVIAVSVGWFFGLSQGNSPLDEGNKNIVLAIFIMIFLYFANVKRTLLIAVYCFVLIFMEELLM
QQIHESIHMADRIALFFMFSVISIIAVRTLHGSIEEKNELIQEIHHRVRNNLQVLSGLVEMHSDSDQGNLRNI
LSDFQNRILAISEVHNYLYKSENYFDIDFSEVIERIIANLIHKFGKQSVKIENLTEQIFLRIEYAIPCAMIFSELL
SNSLKHAFSSDMGKIVIRFHKEGNKYRLQIEDNGSGISDSKTWLKPKTSGFKLIQLLTRQIKGDFQILSDSG
SIAVLEFYT.

FIGURE 3A)

AGAAGGATTAGGTTTCAGGATGTTTAATTTTTTCCCAATACCTAACCAATGGTTTTGAACGTTTTCCTAA
AATCGAAAAATCAAAATCTAAAAATTAAAAAAAATTATTTTTGTAGGTAGGATCACTCCCAATAAAAAACA
GGACGATTTGATCCGCCTTGCATTCGCGTATAAGTCTATAATTTCCGATCAGTTTCAGTTTTATCTCG
CAGGTTTTAGTTCTAAAGAATTATATCTTTATCGGGAAGAATTAGAAAGGATGTTGGACTTTTATGATC
TCAGAAAAAACGTTTTGATCACAGGTTTTCTCTCCGACTTAGAACTAAATTCCCTTTATCAAGAAGCG
GATGCTTTCGTTTCCATGAGTGAACACGAAGGTTTCTGTGTTCCTCTGATCGAAGCCATGATTTATAG
AATTCCGATCCTCGCTTTTTCAGGCGGCGCGGTTTCCGAAACTTTAAACGGAGCCGGTGTTCTTTTT
AAAGAAAAAAATTTTTCCGAACTTGGCTATTTTACTCAATAAAATTTTGACTGATGTTTCTTTCCAAAATC
AAATTTTAACAGGCCAAGATCTACGTCTGAACGAATTTAAAAAAACGGATTATAAATCCGTCCTTAGG
AAGGCACTTGAAATCATCTCTTAA

FIGURE 3B)

MFNFSQYLTNGFERFPKIEKSKSKIKKIIFVGRITPNKKQDDLIRLAFAYKSIISDQFQFYLAGFSSKELYLYR
EELERMLDFYDLRKNVLITGFLSDLELNSLYQEADAFVSMSEHEGFCVPLIEAMIYRIPILAFSGGAVSETL
NGAGVLFKEKNFPNLAILLNKILTDVSFQNQILTGQDLRLNEFKKTDYKSVLRKALEIIS

FIGURE 4A)

GATATCGCCGTGGCGGCCGCATGATTATCAATCACAACCTGAGCGCGGTGAATTCTCACCGTTCTCT
AAAGTTCAACGAGCTTGCTGTGGACAAGACGATGAAGGCTTTGTCTTCCGGTATGCGGATCAATTCC
GTGGCGGACGACGCTTTCGGACTCGCGGTTTCTGAAAAGCTAAGAACGCAGATCAACGGTCTGCGT
CAGGCCGAAAGAAACACCGAAGACGGGATGAGCTTCATTCAAACTGCCGAGGGTTTCCTCGAACAG
ACGTCGAACATCATTCAGAGAATCCGGGTGCTTGCATCCAGACCTCGAATGGTTTCTCAGCAACGAA
AGATTGCATCTTTGGGCAGGTGGGAAGTATTGTGCGCTGGTGGACCAAAGTCCCACCGAATCGCTT
CTCAAGCTGAATTTATAAGTTCAAGCTTTTTAGGGGCAATTCGCAAAAGGTTCACGGGTCGGGTCCA
TGTGGTTTCATATGGGGCCGAACGAAAATCAGCGAGAGAGATTTTACAGCGGCCCGAATGCTTCGA
AAGCCCTGAAGCTTGTAAAGCGGACGGGAGACCGATCGCGATTTCTTCTCCGGAAGAAGCCAACGA
TGTTATCGGTTTAGCGGATGCGGCTCTTACGAGGATCATGAAGCAGAGAGCGGATATGGGGGCTTA
TTACAATAGGCTCGAGTATACCGCAAAAGGGGTGATGGGTGCATATGAAAATATGCAAGCATCGGAA
TCCAGAATTCGGGACGCCGATATGGCGGAGGAAGTTGTCTCGCTGACCACAAAACAAATACTCGTT
CAGAGTGGTACGGCAATGTTAGCGCAGGCAAATATGAAACCGAATTCGGTTCTCAAGCTTCTGCAGC
ATATCTAAATCTAGAACTAGTGGATCGATCCCCAATTCGCCCTATAGTGAGTCGTATTACAATTCACT
GGCCGTCGTTTAACA

FIGURE 4B)

MIINHNLSAVNSHRSLKFNELAVDKTMKALSSGMRINSVADDAFGLAVSEKLRTQINGLRQAERNTEDGM
SFIQTAEGFLEQTSNIIQRIRVLASRPRMVSQQRKIASLGRWEVLCAGGPKSHRIASQAEFISSSFLGAIRK
RFTGRVHVVSYGAERKSAREILQRPECFESPEACKADGRPIAISSPEEANDVIGLADAALTRIMKQRADM
GAYYNRLEYTAKGVMGAYENMQASESRIRDADMAEEVVSLTTKQILVQSGTAMLAQANMKPNSVLKLLQ
HI.

LEPTOSPIRA VACCINE ANTIGENS FOR THE PREVENTION OF LEPTOSPIROSIS

CROSS REFERENCE TO RELATED APPLICATIONS

This application claims the benefit of the U.S. Provisional Application No. 60/113,288, filed Dec. 22, 1998.

FIELD OF THE INVENTION

This invention relates generally to antigenic preparations and specifically to four Leptospira membrane proteins i.e., kinase, permease, mannosyltransferase and endoflagellin which are used to induce a protective immune response in animals. Such proteins can be used immunologically as vaccines for leptospirosis caused by this organism. Alternatively, diagnosis of leptospirosis can be performed by detecting the presence of these proteins, antibody to the proteins, or polynucleotides which encode the proteins.

BACKGROUND OF THE INVENTION

The pathogenic species of the Leptospira genus are the causative agents of leptospirosis, a zoonotic disease of worldwide importance. The bacterium is a gram negative spirochete which thrives under aerobic conditions. These bacteria have fastidious nutritional requirements and are able to utilize long chain fatty acids as a sole source of carbon. Leptospires are motile and their rapid, corkscrew motility serves as a distinguishing identifying feature of this organism. Leptospires are resistant to both metronidazole and 5-fluorouracil, and demonstrate a generation time of 10 to 12 hours in vitro.

All pathogenic Leptospires were formerly classified as *Leptospira interrogans*. Recently DNA homology studies have led to the reclassification of *Leptospira interrogans* into seven pathogenic Leptospira species: *L. borgpetersenii* sv *hardjobovis, L. inadai, L. interrogans, L. kirshneri, L. noguchii, L. santarosai* and *L. weilli*. The serology of pathogenic Leptospira species which are responsible for Leptospirosis disease indicates that there are more than two hundred serovars ("sv") within twenty three serogroups (Farr, R. W. Clin. Infect. Dis. 21:1–8 (1995)). There are many serovars responsible for leptospirosis disease worldwide. *Leptospira interrogans* sv *pomona* is a common isolate from infected swine where it causes fever, jaundice, hemoglobinuria, and renal failure. *Leptospira interrogans* sv *hardjobovis* is an important cause of bovine disease, where it causes abortion and agalactia, and poses a zoonotic threat to humans after prolonged exposure to infected cattle. Many infected animal are asymptomatic. These animals can however act as carriers and shed leptospires through urine.

Leptospira infections in cattle demonstrate a 16% infection rate, with rates being higher in beef cattle than in dairy cattle. The infection rate is also higher in bulls than in cows. There is also a marked prevalence of certain serovars which cause bovine leptospirosis. In a recent survey of cattle in the 48 states in the USA, of those animals positive for leptospira, 84% were infected with sv *hardjobovis,* 12% were infected with sv *pomona,* and 4% were infected with sv *griptotyphosa* (Miller, D. A. et al., Am. J. Vet. res. 52(11):1761–1765 (1991)).

Little is known concerning the pathogenesis of Leptospira infections. Infections are usually transmitted by contact with urine from an infected animal. Soil and water which has been contaminated with infected urine can also transmit infection, although the prolonged survivability of leptospires under these conditions is questionable. Survival of Leptospira outside the host is fostered by a temperature of 22° C. or above, moisture, and a neutral to slightly alkaline environment. Leptospira are readily killed by temperatures above 60° C., detergents, desiccation, and acidity. Once the leptospire has invaded the host; attachment to and penetration of the intercellular junctions of mucosal epithelial cells is a crucial step in the infection. A bacteremia usually results and is the first pathological condition associated with leptospirosis. Once in circulation, the bacterium can colonize the kidneys, where they may cause an acute or chronic infection. Some potential virulence factors involved in the pathogenesis of leptospira are, hyaluronidase, urease, haemolysins, and phospholipases.

Leptospirosis is caused by pathogenic strains of Leptospira which are capable of infecting most mammalian species. The predominant natural reservoirs of pathogenic Leptospira are wild mammals, although other vertebrates occasionally are infected. In addition, several species of leptospires are known pathogens of marine mammals, including Pacific harbor seals (Stampler, M. A. et al., J. Wild. Dis. 34(2):407–410(1989)). Domestic animals such as dogs, cattle, swine, sheep, goats and horses, also may be major sources of human infections. Infection occurs either through direct contact with an infected animal or indirect contact with contaminated soil or water. In livestock, the disease causes economic losses due to abortion, stillbirth, infertility, decreased milk production, and death.

The severity of human leprospirosis varies greatly and is determined to a large extent by the infecting strain and by the general health of the host. The improved ability of regional laboratories to group Leptospira has resulted in the recognition of the large number of serovars endemic in the United States, as well as the extent of infections in a variety of animal species. Nevertheless, it is an infrequently diagnosed human disease. Approximately 100 cases are reported annually in the United States.

Because of its prevalence in rodents and domestic animals, leptospirosis has been primarily a disease of person in occupations heavily exposed to animals and animal products, such as sewer workers, swineherders, veterinarians, abattoir workers, and farmers (Vinetz, J. M., Cur. Opin. Infect. Dis. 10:357–361 (1997)). Also at risk are persons living in rodent-infested housing, such as urban slums, and dog owners. There is a higher incidence in males. At present, the majority of cases occur in the summer and fall in teenagers and young adults. Avocational exposure is now increasingly common.

Common source outbreaks attributed to contaminated ponds or slowly moving streams are numerous. A high attack rate, summer season, young age group, and the proximity of animals to the water typify most of these outbreaks. In some areas of the world, the runoff during flooding also is highly infectious.

Sporadic disease may be acquired by direct contact with infected animals. Vaccination of domestic animals, which prevents clinical disease, may fail to prevent shedding of Leptospira. Pet dogs have been a prominent source of sporadic human cases. The convoluted renal tubules of animal reservoirs harbor viable Leptospira, which are passed in the urine. The duration of asymptomatic urinary shedding varies with the animal species; humans rarely shed Leptospira longer than a few months.

Forms of transmission other than direct and indirect contact with contaminated urine are rare. Lactating animals shed Leptospira in the milk, but whole milk is leptospirocidal after a few hours, and no known human cases have occurred in this manner. Leptospira are not shed in saliva, and animal bites are therefore not a direct source of infection.

The pathogenesis of leptospirosis is very similar to that of other spirochetal diseases, including syphilis (caused by *Treponema pallidum*) and Lymeborreliosis (caused by *Borrelia burgdoferi*). Both syphilis and Lymeborreliosis are characterized by widespread dissemination early in the course of disease, including invasion of the central nervous system. Leptospira share this ability with other pathogenic spirochetes such that meningitis is a common manifestation of leptospirosis. Another feature of spirochetal infections is the ability to persist chronically in the host, as manifested in cases of tertiary syphilis and chronic Lyme arthritis. (For a comprehensive review, see Baranton, G. and Old, I. G., Bull. Inst. Pasteur 93:63–95 (1995)).

Efforts to control leptospirosis have been hampered because virulent leptospires have the capacity for both long-term survival in the environment as well as persistent infection and shedding by wildlife and livestock.

Leptospira membrane proteins are of great importance because they play a key role in bacterial pathogenesis. The identification of membrane proteins involved in Leptospira pathogenesis is significant to understanding not only leptospiral membrane proteins and their involvement in pathogenesis, but also to understanding other spirochetal membrane proteins and their role in pathogenesis.

Currently available leptospiral vaccines produce short-term immunity and do not provide cross-protection against many of the 170 serovars of pathogenic Leptospira (Thiermann, et al., J. Am. Vet. Med. Assoc. 184:722 (1984)). These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide-like substance (LLS) may confer a degree of protection.

In terms of treatment of active infection, oxytetracycline is the drug of choice and is used routinely in the field to both cure infection and carriage. Several vaccine preparations using bacterins or components of lipopolysaccharide have been used with variable success. Protection with the current vaccines tend to be serovar specific and lack the ability to generate a reproducible degree of protection.

SUMMARY OF THE INVENTION

The present invention is based on the identification of four Leptospira membrane proteins ie., kinase, permease, mannosyltransferase and endoflagellin, which are associated with pathogenic strains of Leptospira. Due to spirochetal membrane fragility and the fact that membrane proteins are present in small amounts, there have been limited definitive reports of membrane spanning spirochetal membrane proteins until the present invention. The identification of in vivo expressed genes by mRNA subtractive hybridization is a powerful means by which to identify virulence-related genes. The present invention describes the identification of three *Leptospira interrogans* sv *pomona* genes which are expressed during colonization of the liver of infected Syrian hamsters. The present invention also describes a fourth gene identified from *L. hardjobovis* using a ZAP expression library. The invention also describes four membrane proteins from Leptospira which are immunogenic and useful for inducing an immune response to pathogenic Leptospira as well as providing a diagnostic target for leptospirosis.

BRIEF DESCRIPTION OF THE DRAWINGS

FIGS. 1A and 1B. The complete nucleotide sequence, SEQ ID NO. 5 (FIG. 1A) and deduced amino acid sequence, SEQ ID NO. 1 (FIG. 1B) of Leptospira membrane protein kinase, (ORF1) from pHLE011 and pMW43. The initiation and termination codons are underlined in bold.

FIGS. 2A and 2B. The complete nucleotide sequence, SEQ ID NO. 6 (FIG. 2A) and deduced amino acid sequence, SEQ ID NO. 2 (FIG. 2B) of Leptospira membrane protein permease, (ORF2) from pHLE011 and pMW310. The initiation and termination codons are underlined and in bold.

FIGS. 3A and 3B. The complete nucleotide sequence, SEQ ID NO. 7 (FIG.3A) and deduced amino acid sequence, SEQ ID NO. 3 (FIG. 3B) of Leptospira membrane protein mannosyltransferase, (ORF3) from pMW50. The initiation and termination codons are underlined and in bold.

FIGS. 4A and 4B. The complete nucleotide sequence, SEQ ID NO. 8 (FIG.4A) and deduced amino acid sequence, SEQ ID NO. 4 (FIG. 4B) of Leptospira membrane protein endoflagellin from pDFX210. The initiation and termination codons are underlined and in bold.

DETAILED DESCRIPTION OF THE INVENTION

The present invention provides four immunogenic proteins from the membrane of a pathogenic Leptospira species. These membrane proteins are kinase, permease, mannosyltransferase and endoflagellin. Also included are four polynucleotide sequences which encode these proteins.

The four immunogenic proteins of the present invention are useful in pharmaceutical compositions for inducing an immune response to pathogenic Leptospira.

The invention includes a method of producing these membrane proteins of Leptospira using recombinant DNA techniques. The genes for the four membrane proteins are cloned into plasmid vectors which are then used to transform *E. coli*.

The bacterial genes for these four membrane proteins can likely be derived from any strain of pathogenic Leptospira. Preferably the proteins are from *Leptospira interrogans* sv *pomaona* or *Leptospira borgpetersenii* sv *hardjobovis*. These Leptospira organisms are publically available through the ATCC 10801 University Boulevard, Manassas, Va. 20110-2209 for example.

The invention provides polynucleotides encoding the four Leptospira membrane proteins i.e. kinase, permease, mannosyltransferase and endoflagellin. These polynucleotides include DNA and RNA sequences which encode these four proteins. It is understood that all polynucleotides encoding all or a portion of these four proteins are also included herein, so long as these polynucleotides encode polypeptides that exhibit the function of the native or full length proteins, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement (Wallace, et al., Nucleic Acid Research, 9:879 (1981)).

Alternatively, an expression library can be screened indirectly for the four membrane proteins of the invention having at least one epitope per protein using antibodies to these proteins. Such antibodies can be either polyclonally or monoclonally derived and used to detect expression product indicative of the presence of Leptospira kinase, permease, mannosyltransferase and endoflagellin DNA. Generally, a lambda gt11 library is constructed and screened immunologically according to the method of Huynh, et al., (in DNA Cloning: A Practical Approach, D. M. Glover, ed.,1:49 (1985)).

The development of specific DNA sequences encoding each of the kinase, permease, mannosyltransferase and endoflagellin membrane proteins can also be obtained by:(1) isolation of a double-stranded DNA sequence from the genomic DNA, and (2) chemical manufacture of a DNA sequence to provide the necessary codons for the protein of interest.

The polymerase chain reaction (PCR) technique can be utilized to obtain or amplify the four individual Leptospira membrane proteins from any strain of Leptopira for subsequent cloning and expression of cDNAs encoding these four proteins (e.g., see U.S. Pat. Nos. 4,683,202; 4,683,195; 4,889,818; Gyllensten et al., Proc. Nat'l Acad. Sci. USA, 85:7652–7656 (1988); Ochman et al., Genetics, 120:621–623 (1988) Triglia et al., Nucl.. Acids. Res., 16:8156 (1988); Frohman et al., Proc. Nat'l Acad. Sci. USA, 85:8998–9002 (1988); Loh et al., Science, 243:217–220 (1989)). Similarly, the PCR technique can be routinely used by those skilled in the art, to generate polynucleotide fragments encoding portions of any of the four Leptospiral membrane proteins of the instant invention.

Methods which are well known to those skilled in the art can be used to construct expression vectors containing the four Leptospira membrane proteins or fragments thereof coding sequences and appropriate transcriptional/translational control signals. These methods include in vitro recombinant DNA techniques, synthetic techniques and in vivo recombination/genetic recombination. See, for example, the techniques described in Maniatis et al., Molecular Cloning A Laboratory Manual, Cold Spring Harbor Laboratory, N.Y., Chapter 12 (1982).

A variety of host-expression vector systems may be utilized to express the four Leptospira membrane proteins or fragments thereof. These include but are not limited to microorganisms such as bacteria transformed with recombinant bacteriophage DNA, plasmid DNA or cosmid DNA expression vectors containing a coding sequence for a Leptospira membrane protein or fragment thereof; yeast transformed with recombinant yeast expression vectors containing a coding sequence for a Leptospira membrane protein or fragment thereof, insect cell systems infected with recombinant virus expression vectors (e.g., baculovirus) containing a coding sequence for a Leptospira membrane protein or fragment thereof; or animal cell systems infected with recombinant virus expression vectors (e.g., adenovirus, vaccinia virus) containing a coding sequence for a Leptospira membrane protein or fragment thereof.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedrin promoter may be used; when cloning in mammalian cell systems, promoters such as the adenovirus late promoter or the vaccinia virus 7.5K promoter may be used. Promoters produced by recombinant DNA or synthetic techniques may also be used to provide for transcription of the inserted coding sequence for a Leptospira membrane protein or fragment thereof.

In yeast, a number of vectors containing constitutive or inducible promoters may be used. For a review see, Current Protocols in Molecular Biology, Vol. 2, Ed. Ausubel et al., Greene Publish. Assoc. & Wiley Interscience Ch. 13(1988); Grant et al., Expression and Secretion Vectors for Yeast, in Methods in Enzymology, Eds. Wu & Grossman, Acad. Press, N.Y., Vol. 153, pp. 516–544 (1987); Glover, DNA Cloning, Vol. II IRL Press, Wash., D.C. Ch.3 (1986); and Bitter, Heterologous Gene Expression in Yeast, Methods in Enzymology, Eds. Berger & Kimmel, Acad. Press, N.Y., Vol. 152, pp. 673–684 (1987); and The Molecular Biology of the Yeast Saccharomyces, Eds. Strathern et al., Cold Spring Harbor Press, Vols. I and II (1982). For complementation assays in yeast, cDNAs for Leptospira membrane proteins or fragments thereof may be cloned into yeast episomal plasmids (YEp) which replicate autonomously in yeast due to the presence of the yeast 2 mu circle. Any of the Leptospira membrane protein or fragment thereof sequence may be cloned behind either a constitutive yeast promoter such as ADH or LEU2 or an inducible promoter such as GAL (Cloning in Yeast, Ch. 3, R. Rothstein In; DNA Cloning Vol. 11, A Practical Approach, Ed. D M Glover, IRL Press, Wash., D.C. (1986)). Constructs may contain the 5' and 3' non-translated regions of a cognate Leptospira membrane protein mRNA or those corresponding to a yeast gene. YEp plasmids transform at high efficiency and the plasmids are extremely stable. Alternatively vectors may be used which promote integration of foreign DNA sequences into the yeast chromosome.

A particularly good expression system which could be used to express one of the four Leptospira membrane proteins or fragments thereof is an insect system. In one such system, *Autographa californica* nuclear polyhedrosis virus (AcNPV) is used as a vector to express foreign genes. The virus grows in *Spodoptera frugiperda* cells. The Leptospira membrane protein or fragment thereof coding sequence may be cloned into non-essential regions (for example the polyhedrin gene) of the virus and placed under control of an AcNPV promoter (for example the polyhedrin promoter). Successful insertion of the polyhedrin gene results in production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., J. Biol., 46:586 (1983); U.S. Pat. No. 4,215,051).

In cases where an adenovirus is used as an expression vector, the Leptospira membrane protein or fragment thereof coding sequence may be ligated to an adenovirus transcription/translation control complex, e.g., the late promoter and tripartite leader sequence. This chimeric gene may then be inserted in the adenovirus genome by in vivo or in vitro recombination. Insertion in a non-essential region of the viral genome (e.g., region E1 or E3) will result in a recombinant virus that is viable and capable of expressing a Leptospira membrane protein of fragment thereof in infected hosts. (e.g., See Logan & Shenk, Proc. Natl. Acad. Sci., (USA) 81:3655–3659 (1984)). Alternatively, the vaccinia 7.5K promoter may be used. (e.g., see Mackett et al., Proc. Natl. Acad. Sci., (USA) 79:7415–7419 (1982); Mackett et al., J. Virol., 49:857–864 (1984); Panicali et al., Proc. Natl. Acad. Sci., 79: 4927–4931 (1982)).

Specific initiation signals may also be required for efficient translation of the inserted Leptospira membrane protein or fragment thereof coding sequences. These signals include the ATG initiation codon and adjacent sequences. In cases where the entire Leptospira membrane protein genome, including its own initiation codon and adjacent sequences, are inserted into the appropriate expression vectors, no additional translational control signals may be needed. However, in cases where only a portion of the Leptospiral membrane protein coding sequence is inserted, exogenous translational control signals, including the ATG initiation codon, must be provided. Furthermore, the initiation codon must be in phase with the reading frame of the Leptospiral membrane protein or fragment thereof coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., Methods in Enzymol., 153:516–544 (1987)).

In addition, a host cell strain may be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered Leptospiral membrane protein or fragment thereof may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

The host cells which contain the Leptospira membrane protein or fragment thereof coding sequence and which express the biologically active Leptospira membrane protein or fragment thereof gene product may be identified by at least four general approaches: (a) DNA-DNA hybridization; (b) the presence or absence of "marker" gene functions; (c) assessing the level of transcription as measured by expression of a Leptospiral membrane protein mRNA transcripts in host cells; and (d) detection of Leptospiral membrane protein gene products as measured by immunoassays or by its biological activity.

In the first approach, the presence of the Leptospira membrane protein or fragment thereof coding sequence inserted in the expression vector can be detected by DNA-DNA hybridization using probes comprising nucleotide sequences that are homologous to the Leptospira membrane protein coding sequence or particular portions thereof substantially as described recently (Goeddert et al., 1988, Proc. Natl. Acad. Sci. USA, 85:4051–4055).

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the Leptospira membrane protein or fragment thereof coding sequence is inserted within a marker gene sequence of the vector, recombinants containing the Leptospira membrane protein or fragment thereof coding sequence can be identified by the absence of the marker gene function. Alternatively, a marker gene can be placed in tandem with the Leptospira membrane protein or fragment thereof coding sequence under the control of the same or different promoter used to control the expression of the Leptospira membrane protein coding sequence. Expression of the marker in response to induction or selection indicates expression of the Leptospira membrane protein coding sequence.

In the third approach, transcriptional activity for the Leptospira membrane protein or fragment thereof coding region can be assessed by hybridization assays. For example, RNA can be isolated and analyzed by Northern blot using a probe homologous to the Leptospira membrane protein or fragment thereof coding sequence or particular portions thereof substantially as described (Goeddert et al., 1988, Proc. Natl. Acad. Sci. USA, 85:4051–4055). Alternatively, total nucleic acids of the host cell may be extracted and assayed for hybridization to such probes.

In the fourth approach, the expression of the Leptospira membrane protein or fragment thereof product can be assessed immunologically, for example by Western blots, immunoassays such as radioimmunoprecipitation, enzyme-linked immunoassays and the like.

Once a recombinant that expresses a Leptospira membrane protein or fragment thereof is identified, the gene product should be analyzed. This can be achieved by assays based on the physical, immunological or functional properties of the product.

A Leptospira membrane protein or fragment thereof should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

DNA sequences encoding the four membrane proteins of the invention can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the genes for the expression of the four Leptospira membrane proteins of the invention. Prokaryotic hosts may include Gram negative as well as Gram positive bacteria, such as *E. coli, S. typhimurium,* and *Bacillus subtilis.*

A recombinant DNA molecule coding for the four Leptospira membrane proteins of the invention can be used to transform a host using any of the techniques commonly known to those of ordinary skill in the art. Especially preferred is the use of a plasmid containing any of the four Leptospira membrane protein coding sequences for purposes of prokaryotic transformation. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

In the present invention, any of the four Leptospira membrane protein encoding sequences may be inserted into a recombinant expression vector. The term "recombinant expression vector" refers to a plasmid, virus or other vehicle known in the art that has been manipulated by insertion or incorporation of any of the four Leptospira membrane protein genetic sequences. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported (Heinemann, et al., Nature, 340:205 (1989); Rose, et al., Gene, 60:237 (1987)). Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of any of the four Leptospira membrane proteins in prokaryotic hosts.

Examples of promoters which can be used in the invention are: rec A, trp, lac, tac, and bacteriophage lambda p[R] or p[L]. Examples of plasmids which can be used in the invention are listed in Maniatis, et al., (Molecular Cloning, Cold Spring Harbor Laboratories, 1982).

Antibodies provided in the present invention are immunoreactive with any of the four Leptospira membrane proteins. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495 (1975); Current Protocols in Molecular Biology, Ausubel, et al., ed., (1989)).

The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to any of the four Leptospira membrane proteins of the invention can be prepared using an intact polypeptide or fragments containing small peptides of interest as the immunizing antigen.

Any of the proteins or fragments thereof of SEQ ID NOS: 1–4 can also be produced by chemical synthesis of the amino acid sequence of any of these four proteins (Goeddert et al., Proc. Natl. Acad. Sci. USA,85:4051–4055 (1988)), as predicted from the cloning and sequencing of a cDNA coding for any of these four Leptospira membrane proteins. The four Leptospira membrane proteins may be chemically synthesized using standard peptide synthesis methods known in the art. These methods include a solid-phase method devised by R. Bruce Merrifield, (Erickson and Merrifield, "Solid-Phase Peptide Synthesis", in The Proteins, Volume 2, H. Neurath & R. Hill (eds.) Academic Press, Inc., New York pp. 255–257; Merrifield, "Solid phase synthesis", Science, 242:341–347 (1986)). In the solid-phase method, amino acids are added stepwise to a growing peptide chain that is linked to an insoluble matrix, such as polystyrene beads. A major advantage of this method is that the desired product at each stage is bound to beads that can be rapidly filtered and washed and thus the need to purify intermediates is obviated. All of the reactions are carried out in a single vessel, which eliminates losses due to repeated transfers of products. This solid phase method of chemical peptide synthesis can readily be automated making it feasible to routinely synthesize peptides containing about 50 residues in good yield and purity (Stewart and Young, Solid Phase Peptide Synthesis, 2nd ed., Pierce Chemical Co. (1984); Tam et al., J. Am. Chem. Soc., 105:6442 (1983)).

Any of the proteins or fragments thereof of SEQ ID NOS: 1–4 used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which any of the four proteins or a fragment thereof of any of the four proteins to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Minor modifications of primary amino acid sequence of any of the four proteins of the invention may result in proteins which have substantially equivalent function compared to the native Leptospira proteins described herein. Such modifications may be deliberate, as by site-directed mutagenesis, or may be spontaneous. All proteins produced by these modifications are included herein as long as native function exists i.e., binds to antibody specific to the any of the four Leptospira membrane proteins.

Modifications of primary amino acid sequence of any of the four membrane proteins also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted protein or fragment thereof also immunoreact with the unsubstituted protein or fragment thereof.

Isolation and purification of microbially expressed protein, on fragments thereof, provided by the invention, may be carried out by conventional means including preparative chromatography and immunological separations involving monoclonal or polyclonal antibodies.

The invention extends to any host modified according to the methods described, or modified by any other methods, commonly known to those of ordinary skill in the art, such as, for example, by transfer of genetic material using a lysogenic phage, and which result in a prokaryote expressing any of the four Leptospira genes for membrane proteins kinase, permease, mannosyltransferase or endoflagellin. Prokaryotes transformed with any of the four Leptospira genes encoding the four membrane proteins of the invention are particularly useful for the production of polypeptides which can be used for the immunization of an animal (e.g., a rabbit).

In one embodiment, the invention provides a pharmaceutical composition useful for inducing an immune response to pathogenic Leptospira in an animal comprising an immunologically effective amount of any one of the four Leptospira membrane proteins in a pharmaceutically acceptable carrier. The term "immunogenically effective amount," as used in describing the invention, is meant to denote that amount of Leptospira antigen which is necessary to induce in an animal the production of an immune response to Leptospira. The four Leptospira membrane proteins of the invention are particularly useful in sensitizing the immune system of an animal such that, as one result, an immune response is produced which ameliorates the effect of Leptospira infection.

Any of the four Leptospira membrane proteins of the invention can be administered parenterally by injection, rapid infusion, nasopharyngeal absorption, dermal absorption, and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing any of the four Leptospira membrane proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal (including a human) being immunized. Adjuvants can be loosely divided into several groups based on their composition.

These groups include oil adjuvants (for example, Freund's Complete and Incomplete), mineral salts (for example, $AlK(SO_4)2$, $AlNa(SO_4)2$, $AlNH4(SO_4)$, silica, alum, $Al(OH)3$, $Ca_3 (PO_4)2$, kaolin, and carbon), polynucleotides (for example, poly IC and poly AU acids), and certain natural substances (for example, wax D from *Mycobacterium tuberculosis,* as well as substances found in *Corynebacterium parvum, Bordetella pertussis,* and members of the genus Brucella).

In another embodiment, a method of inducing an immune response to pathogenic Leptospira in an animal (including a human) is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Leptospira is desirable include swine, cattle and humans.

Generally, the dosage of any of the four Leptospira membrane proteins of the invention administered to an animal (including a human) will vary depending on such factors as age, condition, sex and extent of disease, if any, and other variables which can be adjusted by one of ordinary skill in the art.

The antigenic preparations of the invention can be administered as either single or multiple dosages and can vary from about 10 ug to about 1,000 ug for any of the four Leptospira membrane protein antigen per dose, more preferably from about 50 ug to about 700 ug antigen per dose, most preferably from about 50 ug to about 300 ug antigen per dose. When used for immunotherapy, the monoclonal antibodies of the invention maybe unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., Science, 231:148 (1986)) and can be selected to enable drug release from the monoclonal antibody molecule at the target site. Examples of therapeutic agents which can be coupled to the monoclonal antibodies of the invention for immunotherapy are drugs, radioisotopes, lectins, and toxins. The labeled or unlabeled monoclonal antibodies of the invention can also be used in combination with therapeutic agents such as those described above.

Especially preferred are therapeutic combinations comprising the monoclonal antibody of the invention and immunomodulators and other biological response modifiers. When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the disorder, the condition of the patient and half-life of the agent.

The dosage ranges for the administration of monoclonal antibodies of the invention are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

In a further embodiment, the invention provides a method of detecting a pathogenic Leptospira-associated disorder in an animal (including a human) comprising contacting a cell component with a reagent which binds to the cell component. The cell component can be nucleic acid, such as DNA or RNA, or it can be protein. When the component is nucleic acid, the reagent is a nucleic acid probe or PCR primer. When the cell component is protein, the reagent is an antibody probe.

The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for any of the four Leptospira proteins of the invention may be used to detect the presence of that protein (using antibody) or polynucleotide (using nucleic acid probe) in biological fluids or tissues. Any specimen containing a detectable amount any of the four Leptospira membrane protein antigens or polynucleotides can be used. A preferred specimen of this invention is blood, urine, cerebrospinal fluid, or tissue of endothelial origin.

When the cell component is nucleic acid, it may be necessary to amplify the nucleic acid prior to binding with a Leptospira specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, any of the four Leptospira membrane proteins of the invention can be used to detect antibodies to any one of those four proteins in a specimen. The four Leptospira membrane proteins of the invention are particularly suited for use in immunoassays in which it can be utilized in liquid phase or bound to a solid phase carrier. In addition, any one of the four Leptospira membrane proteins used in these assays can be detectably labeled in various ways.

Examples of immunoassays which can utilize any one of the four membrane proteins of the invention are competitive and noncompetitive immunoassays in either a direct or indirect format. Examples of such immunoassays are the radioimmunoassay (RIA), the enzyme-linked immunosorbant assay, the sandwich (immunometric) assay, a precipitin reaction, a gel immunodiffusion assay, an agglutination assay, a fluorescent immunoassay, a protein A immunoassay and an immunoelectrophoresis assay, and the Western blot assay. Detection of antibodies which bind to any one of the four Leptospira membrane proteins of the invention can be done utilizing immunoassays which run in either the forward, reverse, or simultaneous modes, including immunohistochemical assays on physiological samples. The concentration of the Leptopira membrane protein which is used will vary depending on the type of immunoassay and nature of the detectable label which is used. However, regardless of the type of immunoassay which is used, the concentration of the Leptospira membrane protein utilized can be readily determined by one of ordinary skill in the art using routine experimentation.

Any one of the four Leptospira membrane proteins of the invention can be bound to many different carriers and used to detect the presence of antibody specifically reactive with the protein.

Examples of well-known carriers include glass, polystyrene, polyvinyl chloride, polypropylene, polyethylene, polycarbonate, dextran, nylon, amyloses, naturaland modified celluloses, polyacrylamides, agaroses, and magnetite. The nature of the carrier can be either soluble or insoluble for purposes of the invention.

Those skilled in the art will know of other suitable carriers for binding any one of the four Leptospira membrane proteins of the invention or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to any one of the Leptospira membrane proteins of the invention may be present in various biological fluids and tissues. Any sample containing a detectable amount of antibodies to any one of the four Leptospira membrane proteins can be used. Normally, a sample is a liquid such as urine, saliva, cerebrospinal fluid, blood, serum and the like, or a solid or semi-solid such as tissue, feces and the like. The monoclonal antibodies of the invention, directed toward any one of the four Leptospira membrane proteins of the invention, are also useful for the in vivo detection of antigen. The detectably labeled monoclonal antibody is given in a dose which is diagnostically effective. The term "diagnostically effective" means that the amount of detectably labeled monoclonal antibody is administered in sufficient quantity to enable detection of any one of the four Leptospira membrane protein antigens for which the monoclonal antibodies are specific.

The concentration of detectably labeled monoclonal antibody which is administered should be sufficient such that the binding to those cells, body fluid, or tissue having any one of the four Leptospira membrane proteins is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the animal (including a human). The dosage of monoclonal antibody can vary from about 0.001 mg/m$^2$ to about 500 mg/m$^2$, preferably 0.1 mg/m$^2$ to about 200 mg/m$^2$ most preferably about 0.1 mg/m$^2$ to about 10 mg/m$^2$. Such dosages may vary for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of Leptospira associated disorder. Thus, by measuring the increase or decrease of any one of the four Leptospira membrane proteins of the invention or antibodies to the any one of the four Leptospira membrane proteins present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a binding reagent to any one of the four Leptospira membrane proteins, such as an antibody. A second container may further comprise any one of the four Leptospira membrane proteins recognized by such antibody. The constituents may be present in liquid or lyophilized form, as desired.

The following examples are intended to illustrate but not limit the invention. While they are typical of those that might be used, other procedures known to those skilled in the art may alternatively be used.

EXAMPLES

The following examples describe the identification of four Leptospira membrane proteins i.e. kinase, permease, mannosyltransferase and endoflagellin as important leptospiral proteins that are produced during active Leptospiral infection of an animal. The methods by which these genes were cloned and sequenced is described. Sequence analysis and homology studies are shown, further indicating that these proteins are membrane proteins of pathogenic Leptospira and therefore are excellent vaccine candidates.

Example 1

Bacterial Strains and Growth Conditions

*Leptospira interrogans* sv *pomona* strain 2966 and *Leptospira borgpetersenii* sv *hardjobovis* Hb197 was obtained from freezer stocks of an original bovine field isolate. All leptospira in vitro cultures were propagated at 30° C. in PLM-5 broth. *Escherichia coli* strain DH5a was propagated in Luria-Bertani medium, with or without 100 μg/ml ampicillin, or 50 μg/ml kanamycin. *E. coli* strain LE392 was utilized in the construction and amplification of the genomic minibank library. All *E. coli* cultures were propagated at 37° C. In some cases (pDFX210, ORF1) expression of heterologous cloned proteins in an *E. coli* host was done using the pL heat shock promoter. Under these circumstances, the strain was initially propagated at 30° C. in 2x yeast tryptone medium until an optical density (695 nm) of 0.5 was reached. The culture was shifted to 42° C. to induce protein expression.

Animal Passage of *L. interrogans* sv *pomona* and *L borgpetersenii* sv *hardjobovis* Hb197

Animal passage of virulent cultures were done in Syrian hamsters using liver homogenates of the infected animals as an inoculum for subsequent passage. A total of 0.2 cc of a $10^{-1}$ dilution of infected liver homogenate in Stuart's Medium or PLM-5 supplemented with 0.1% agarose was used to inoculate hamsters for passage by subcutaneous (*L. pomona*) and intraperotoneal (*L. hardjobovis*) routes of administration. Microscopic examination of liver homogenate smears were done to confirm the presence of spirochetes.

Extraction and Purification of Bacterial mRNA from Infected Hamster Liver

The Leptospira infected hamsters were euthanised by $CO_2$ followed by cervical dislocation. The livers were harvested by necropsy and washed twice with ice cold PBS. The livers were resuspended in 10 ml PBS (room temperature) to which an equal volume of 4M guanidine isothiocyanate in 50 mM sodium citrate, 0.1% sodium docecyl sulfate was added. This suspension was incubated on ice with intermitted vortexing until the tissue was visibly disassociated water-saturated phenol (pH 5.2) was immediately added to facilitate the removal of DNA. This mixture was vortexed for one minute, then centrifuged at 10,000xg at room temperature for 30 minutes. The aqueous phase, which contains the nucleic acids, was extracted twice with TRIS-buffered phenol (pH 8.0): chloroform: isoamyl alcohol (25:24:1). This predominantly RNA-containing aqueous phase was precipitated by the addition of 0.1 volume of 3 M sodium acetate (pH 4.5) and 2.5 volumes of 95% ethanol and incubated overnight at –20° C. The precipitated nucleic acids were pelleted and washed. To further facilitate the removal of remaining DNA, the pellet was extracted in 5 ml of 3 M sodium acetate (pH 6.0). The extraction was repeated until the nucleic acid pellet was transparent. The quality and quantity of the RNA was determined spectrophotometrically by examining the absorbance ratios at 254 nm/280 nm, and at 260 nm/230 nm.

The eukaryotic mRNA was removed from the preparation with an oligo dT cellulose column using the FastTrack mRNA isolation kit (Invitrogen Corporation) with a modification of the manufacturer's instructions. Briefly, the concentration NaCl concentration of the RNA preparation was adjusted to 0.5 M using 5 M NaCl. The preparation was then added to 50 mg of oligo dT cellulose that had been pre-equilibrated with 1 ml of the kit's binding buffer. The mixture was incubated for 60 minutes at room temperature with frequent, gentle mixing. Following incubation, the oligo dT cellulose was pelleted at room temperature by centrifugation at 2,000xg for 10 minutes. The supernatant, containing the bacterial mRNA was removed and precipitated by the addition of 0.1 volume sodium acetate (pH 4.5), 2.5 volumes of 95% ethanol, and incubated overnight at –20° C. The bacterial mRNA was stored in this fashion until needed.

Total bacterial RNA was isolated from PLM-5 propagated strain following incubation for 96 hours at 30° C. Bacterial cells were removed from the agar by scraping, and washed four times in ice cold PBS. the RNA was isolated as described above, without the oligo dT cellulose extraction.

cDNA Synthesis

The bacterial mRNA isolated from the infected livers or the PLM-5 propagated cultures were used as templates for the synthesis of double-stranded cDNA using avian meoblastosis virus (AMV) reverse transcriptase and the RiboClone cDNA synthesis system (Promega Corporation, Madison, Wis. USA) following the manufacturer's instructions. The newly synthesized cDNA was treated with DNase-free RNase for 30 minutes at 37° C., extracted once with phenol: chloroform: isoamyl alcohol, and precipitated. The second strand was synthesized immediately following the first strand synthesis according to the manufacturer's instructions.

The cDNA derived from the PLM-5 propagated bacteria was biotinylated using the BioNick Labeling System ( BRL Life technologies, Gaithersburg, Md.) following the manufacturers' instructions.

In preparation for the subtractive hybridization, the ds cDNA preparations were denatured by incubation at 95° C. for 5 min, followed by rapid chilling in an ice bath.

Subtractive Hybridization

The technique of subtractive hybridization was used to isolate the four Leptospira genes of the instant invention (Uft, E. A., et al., Can. J. Microbiol. 41:152–156 (1995)). This technique can be used for isolating a particular mRNA when there are two cell types, one of which expresses the RNA and the other of which does not. In the present invention, it was determined that certain Leptospira genes were turned on and expressed during active infection of this microorganism in a hamster model. These four genes are not expressed when Leptospira is grown in culture media. The mRNA from livers of Leptospira infected hamsters ("target or Vir$^+$ cells") is used as substrate to prepare a set of cDNA molecules corresponding to all the expressed genes. To remove sequences that are not specific for the target cells, the cDNA preparation is exhaustively hybridized with the mRNA of Leptospira grown in culture media ("Vir$^-$ cells"). This step removes all the sequences from the cDNA preparation that are common to the two cell types. After discarding all the cDNA sequences that hybridize with the other mRNA, those that are left are hybridized with the mRNA from the target cell to confirm that they represent coding sequences. These clones contain sequences specific to the mRNA population of the Vir$^+$ cells.

For the subtractive hybridization, a total of 50 μg of denatured in vivo bacterial cDNA from the liver extract (Vir+) was hybridized with 250 μg denatured biotinylated cDNA from the PLM-5 propagated (Vir–) in a hybridization buffer containing 20 mM TRIS, 0.6 M NaCl, 2 mM EDTA, and 0.2% sodium dodecyl sulfate (final concentration). The hybridization proceeded at a constant temperature of 70° C. for 48 hours. The 1:4 ratio of the two cDNA populations helped to ensure the formation of cDNA hybrids for all common transcriptional species.

Selective removal of all double-stranded biotinylated cDNA hybrids was done by incubation of the hybridization mixture with streptavidin—coated paramagnetic beads (Dynal, Inc.). A total of 2001 µl Dynal streptavidin beads were placed in a 1.5 ml eppendorf tube and washed 3 times with 2× Dynal binding buffer (10 mM TRIS (pH 7.5), 1 mM EDTA, 2.0 M NaCl. After the final wash the beads were resuspended in 200 µl 2× binding buffer, to which an equal volume of the subtractive hybridization mixture was added. This was incubated on a platform rotator at room temperature for 15 min at 85 rpm. Following incubation, the paramagnetic bead—bound biotinylated cDNA hybrids were removed by magnetic extraction according to Dynal's instructions. Nucleic acids in the remaining supernatant were precipitated by the addition of 0.1 volume 3M sodium acetate (pH 5.3) and 0.8 volume isopropyl alcohol.

The cDNA products that remained in the supernatant putatively represent the differences in gene expression between the liver propagated and PLM-5 propagated *L. interrogans*. These products are subsequently referred to as subtraction products.

Amplification of the Subtractive Hybridization Products

The double stranded cDNA subtraction products were restriction endonuclease digested with Sau3A, and then ligated to tandem, 21-mer PCR primer adapters. The adapters, AUS 1, SEQ. ID. NO.: 9 (5' GATCGGACGGTGAATTCTCGAGAGTG 3'), and AUS 2, SEQ. ID. NO.: 10 (5' GACACTCTCGAGAATTCACCGTCC 3') both have Sau3A sites, are phosphorylated, and were annealed to each other by heating to 94° C. and cooled to room temperature (25° C.) prior to ligation to the subtraction products. The AUS 2 complementary primer was used in the subsequent PCR amplification step. PCR reaction conditions were 10 mM Tris-HCl (pH 8.0), 50 mM KCl, 2.5 mM $MgCl_2$, 10 mM each dNTP, 1 pmole AUS 2, and 10 units Taq DNA polymerase (all final concentrations). The total reaction volume was 100 ml. A Perkin-Elmer Cetus model 9600 thermocycler was utilized using the following program, with rapid temperature ramping: 94° C., 60 sec; 37° C., 30 sec; 55° C., 60 sec; for a total of 35 cycles.

Isolation and Identification of Differentially Expressed Genomi Loci

Plasmids pUC18 and pGEMT EASY were used as vectors for cloning into *E. coli* DH5a. All minibank library constructions, transfections, electroporations, plasmid isolation, restriction endonuclease digestions, and other genetic manipulations, were done according to standard methods (Maniatis, et al., 1982).

The PCR subtraction products were directly cloned into the commercial pGEMT—Easy vector (Promega). Positive clones were screened on X-Gal ampicillin Luria Bertani plates, and the cloned inserts were analyzed by DNA sequencing (Advanced Genetics Analysis Corporation, Minneapolis, Minn.). DNA sequences were identified by sequence database searches using the BLAST algorithm. One clone, pHLE001 displayed homology to several bacterial membrane bound histidine kinase genes. Since the subtraction product represented a partial gene, this clone, was labeled with digoxigenin (DIG) using the Genius System (Boehreinger Mannheim Biochemicals, Indianapolis, Ind., USA) according to the manufacturer's instructions. The subtraction product was then used as a probe in a Southern hybridization of EcoRI restriction endonuclease digested *Leptospira interrogans* sv *pomona* (*Leptospira pomona*) genomic DNA. The pHLE001 probe hybridized to a 1200 bp fragment. An EcoRI genomic minibank in the 800 bp to 2,500 bp size range was generated and used to recover the 1,200 bp fragment. This fragment was cloned into plasmid pUC18 and was designated pHLE 011. This clone was later determined to contain elements of both ORF1 and ORF2.

Separate protein expression vectors were used to express the identified ORFs to levels sufficient to small scale protein purification and vaccine protection studies.

Additional cloning was accomplished using the Vectorette strategy (Genosys, Woodlands, Tex.) This strategy was employed to walk through EcoRI Vectorette genomic libraries and find the remaining portions of the genes. Briefly specific primers were designed from the known sequenced portions to walk both upstream and downstream of the original PCR product. This strategy resulted in the amplification of fragments from several subtraction—derived PCR primers. These clones and their putative identities are summarized in table 1.

DNA sequence analysis of the cloned 1200 bp insert was accomplished using the dideoxy chain termination method of Sanger using the Applied Biosystems automated DNA sequencer.

DNA sequence analysis of the pHLE011. clone using the DNASTAR program revealed two open reading frames (ORFs). The frames designated ORF1, ORF2 and ORF3 consist of 603 bp, 1131 bp and 618 bp, respectively.

TABLE 1

Subtractive hybridization clone identified in this study.

| Clone | Vector | Insert Size | Sequence |
|---|---|---|---|
| pHLE011 | pUC18 | 1,200 bp | ORF1/ORF2 |
| pMW43 | pFLEX10 | 1110 bp | ORF1 |
| pMW310 | pFLEX10 | 1150 bp | ORF2 |
| pMW48 | pFLEX10 | 680 bp | ORF3 |

Vectorette Library Construction and Screening

Vectorette PCR (Genesys Inc.) following the manufacturers' instructions was employed in an attempt to isolate the remaining portions of both ORFs. Briefly, PCR primers were designed for the 5' end of ORF1 to extend upstream. For ORF2, primers were designed for the 3' end of ORF2 to extend downstream. Vectorette libraries were generated using Pvull, HindIII, Hpal,Rsa1,EcoR1,Ssp1, Dra1, or Mfel restriction digestion of the *L. interrogans* genomic DNA, followed by ligation to the specific Vectorette primer binding site at one end, according to the manufacturers' directions . Vectorette PCR using the above libraries resulted in the generation of several products of various lengths. DNA sequence analysis of the specific products were used to aligned the sequences and allow for the completion of ORF2 and truncated version of ORF1. The subtraction clones are outlined in table 1.

λZAP Phage Genomic Library Construction and Screening

A complete Bm HI genomic library of *L. borgpetersenii* sv *hardjobovis* was constructed as a custom library package by Stratagene (La Jolla, Calif., USA) using the ZAP Express vector. It was this library from which the endoflagellin protein was identified.

The library was titered and amplified according to the manufacturers directions using *Escherichia coli* XL1-Blue MRF'. Following the appearance of plaques, dry nylon filters (Nytran) which had been pre-soaked in 5 μM IPTG were placed onto the plates and incubated inverted overnight at 37° C.

Following overnight incubation, the plates were chilled for one hour at 4° C. Filters were then lifted and washed three times in PBST. The filters were then blocked by incubation for one hour at room temperature in PBST/3% non-fat dry milk. After washing the blocked filters three times in PBST, immune rabbit antiserum was added to each filter at a 1:5,000 dilution in PBST. The primary antibody was incubated with the filters for three hours at 37° C. Filters were then washed three times, five minutes each, with PBST, and the secondary anti-rabbit alkaline phosphatase conjugate antibody was added at 1:5,000 dilution. Filters were incubated at 37° C. for two hours. Following incubation with the secondary antibody, the filters were once with PBST for five minutes, followed by two, five minute washes in PBS. Positive plaques were visualized by immersing the filters in BCIP solution for one minute at room temperature.

Isolation and Identification of λZAP Phage Library Clones

A total of fourteen plaques reacted strongly with the immune rabbit antisera. Each of these positive phage were converted to phagemids and transformed into *Escherichia coli* XLOR cells for plasmid isolation and amplification. Each of these clones and their insert size is outlined in table 2.

Positive plaques were excised and converted to phagemids in vivo using the method supplied from the manufacturer.

TABLE 2

λZAP Expression library clones identified in this study.

| Clone | Vector | Insert Size | ORF |
|---|---|---|---|
| pDFX210 | pFLEX10 | 900 bp | endoflagellin |

Northern Analysis

Samples of bacterial RNA were analyzed in a Northern hybridization using the $^{32}$P-labeled 3.2 kb cloned fragment from pHLE011 as a probe. For the Northern hybridizations all probes were labeled with $^{32}$P using the Multiprime DNA Labeling Kit (Amersham International Pic, Amersham, UK) following the manufacturer's instructions. Hybridization conditions were: 5×SSC, 50% formamide, 0.02% SDS, 0.1% N-lauroylsarcosine, 2% sheared salmon sperm DNA, and 20 mM sodium maleate (pH 7.5). The hybridization proceeded at 42° C. for 16 hours. Stringency washes were: twice with 2×SSC, 0.1% SDS for five minutes at room temperature, and twice with 0.5×SSC, 0.1% SDS for 15 minutes at 55° C. Signals were visualized by autoradiography.

DNA Sequence Analysis

Double stranded, bi-directional DNA sequence analysis for selected clones was performed using the ABI200 PRISM System (dye terminator) by LARK (The Woodlands, Texas, USA).

DNA and Primary Sequence Analysis

DNA sequence analysis of the three subtractive hybridization clones identified three major open reading frames (ORF). The original subtraction clone pHLE011 contained two partial ORFs, designated ORF1 and ORF2. Using these partial sequences, Vectorette PCR was used to complete both ORF1 and ORF2 sequences, which were subsequently subcloned into PFLEX10 to yield pMW43 (FIG. 1) and pMW310 (FIG. 2) respectively. DNA sequence analysis of a separate subtraction clone, pHLE004, identified another major ORF designated ORF3. This partial sequence was used to design PCR primers for Vectorette PCR. This completed the ORF3 sequence (FIG. 3).

The primary sequence for all three ORFs was deduced using the DNASTAR software package. The deduced primary sequences for the three ORFs identified putative proteins having molecular weights of 41,000 Da, 43,000 Da, and 25,000 Da, respectively. The entire ORF of the endoflagellin gene proved to be 849 bp in length. The deduced primary sequence was a protein of 283 amino acids having a calculated molecular weight of 32,000.

Sequence Database Analysis

A similarity search of these four Leptospira sequences was performed against the sequence databases through the National Center for Biotechnology (NCBI) BLAST E-mail server. The BLASTn and BLASTx sequence analysis algorithms were employed in an attempt to identify DNA and primary sequence homologies. Putative gene identities are outlined in Table 3.

TABLE 3

BLAST database homologies of the cloned potential antigens identified from this study.

| CLONE | GENE | HOMOLOGY |
|---|---|---|
| pMW43 | ORF1 | membrane kinase |
| pMW310 | ORF2 | membrane permease |
| pMW50 | ORF3 | mannosyltransferase |
| pDFX210 | endoflagellin | endoflagellin |

Example 2

Syrian Hamster Leptospirosis Challenge Model

Female Syrian hamsters, ranging from one to four months in age, are used in all bacterial passages and challenges. For the sv *pomona* challenge model hamsters are infected by the subcutaneous route using 0.2 ml liver homogenate containing viable bacteria as determined by phase contrast microscopy. Dilution rates of bacteria range from 1:1000 ($4\times10^5$ bacteria/ml to 1:10 ($4\times10^7$ bacteria/ml).

For the *hardjobovis* challenge, hamsters are infected by the intraperotoneal route using 0.5 ml liver homogenate containing viable bacteria as determined by phase contrast microscopy. Dilution rates of bacteria range from 1:1000 ($4\times10^5$ bacteria/ml) to 1:10 ($4\times10^7$ bacteria/ml).

Hamster liver tissue containing the viable leptospires are surgically excised following necropsy and processed as follows. Approximately one gram of tissue is placed in a glass dounce homogenizer. A total of nine milliliters of PLM-5 supplemented with 0.1% agarose is then added to the tissue. The tissue is then homogenized to a uniform consistency. This represents a $10^{-1}$ dilution of bacteria. All subsequent dilutions are made using the PLM-5 diluent.

Recombinant Protein Expression

Depending upon the expression vector used, proteins were induced using heat shock for the PL promoter plasmid or IPTG using the lacZ promoter plasmid. All protein expression was done in *E. coli* DH5α (lacZ) or *E. coli* LE392(PL) while propagation was done in 2×yeast tryptone broth (2×YT broth).

Briefly, cultures using lacZ expression were propagated at 37° C. until an optical density (at 695 nm) of 0.4 to 0.5 was achieved. Recombinant proteins were induced by the addition of 1 mM IPTG (isopropylthio-β-D-galactopyranoside). Incubation was continued from anywhere between two to 12 hours, depending upon the expected protein yield.

Constructs using the PL promoter system were propagated at 30° C. until an optical density (at 695 nm) of 0.4 to 0.5 was achieved. Recombinant proteins were induced by shifting the culture temperature to 42° C. and continuing the incubation for two to four hours. Bacterial cells were harvested by centrifugation at 8,000×G for 15 minutes at 4° C. Cells were lysed by two passes through a French pressure cell at 20,000 psi. Bacterial debris was removed by centrifugation at 20,000×G and the supernatants stored at −20° C. until needed.

Protein extracts were assayed by SDS-PAGE according to standard methods (ref).

Protective Efficacy Data of Experimental Vaccine Antigens in the Hamster Leptospirosis Model Protein extracts from the recombinant clone containing pHLE011 protected 4/6 hamsters (67%) from lethal infection in the sv *pomona* infection model. Purified recombinant protein from pMW43, contain only ORF1 from pHLE011, protected 2/6 hamsters (33%) from lethal infection in the sv *pomona* infection model. The purified recombinant protein from pDFX210 did not provide any protection against the sv *pomona* infection. The protective potential of each of these antigens in the sv *hardjobovis* model is underway. Table 4 summarizes the vaccine challenge results for all the antigens tested.

For experimental vaccinations, the animals are vaccinated twice, two weeks apart, with ca: 5 μg of the experimental protein. At two weeks following the last vaccination, the animals are challenged with either serovar using the procedure outlined above.

TABLE 4

Protective potential of selected antigens against lethal leptospira challenge in the Syrian hamster challenge model of Leptospirosis.

| Antigen clone | Source | Pomona Protection | Hardjobovis Protection |
|---|---|---|---|
| pHLE011 | subtraction library | 67% | — |
| pMW43 | ORF1 (pHLE011) | 33% | — |
| pDFX210 | phage library | 0% | 100% |

SEQUENCE LISTING

```
<160> NUMBER OF SEQ ID NOS: 8

<210> SEQ ID NO 1
<211> LENGTH: 201
<212> TYPE: PRT
<213> ORGANISM: Leptospira interrogans as pomona

<400> SEQUENCE: 1

Met Arg Ser Val Gln Glu Lys Asn Glu Leu Ile Gln Glu Ile His His
1               5                   10                  15

Arg Val Arg Asn Asn Leu Gln Val Ile Ser Gly Leu Val Glu Met His
            20                  25                  30

Ser Gly Ser Gly Lys Glu Asn Leu Gln Ile Ile Leu Ser Asp Phe Gln
        35                  40                  45

Asn Arg Ile Leu Ala Ile Ser Glu Val His Asn Tyr Leu Tyr Lys Ser
    50                  55                  60

Glu Asn Tyr Phe Glu Ile Asp Phe Val Glu Val Met Asp Lys Ile Ile
65                  70                  75                  80

Leu Asn Leu Ser Tyr Arg Leu Gly Lys Arg Ser Ile Lys Ile Glu Thr
                85                  90                  95

Glu Ala Glu Ser Thr Phe Leu Arg Ile Glu Asn Ala Ile Pro Cys Ala
            100                 105                 110

Met Ile Phe Asn Glu Leu Leu Ser Asn Ser Leu Lys His Ala Phe Arg
        115                 120                 125

Ser Glu Leu Gly Thr Val Gln Ile Ser Phe Arg Lys Lys Gly Asp Lys
    130                 135                 140

Tyr Tyr Leu Gln Val Ser Asp Asn Gly Ser Gly Ile Lys Asp Phe Lys
145                 150                 155                 160

Ile Trp Ser Lys Pro Lys Thr Ala Gly Phe Thr Leu Ile Gln Ile Leu
```

```
                    165                 170                 175
Thr Lys Gln Ile Lys Gly Arg Phe Gln Ile Phe Ser Glu Gly Gly Phe
            180                 185                 190

Thr Ala Val Leu Glu Phe Asn Ser Ile
            195                 200

<210> SEQ ID NO 2
<211> LENGTH: 377
<212> TYPE: PRT
<213> ORGANISM: Leptospira interrogans sv pomona

<400> SEQUENCE: 2

Met Lys Phe Ser Gly Leu Thr Asn His Ile Tyr Lys Asp Arg Asp Tyr
1               5                   10                  15

Leu Thr Arg Asn Arg Ala Phe His Leu Phe Ile Phe Asn Val Val Ser
            20                  25                  30

Leu Leu Leu Gly Leu Ser Val Asn Phe Tyr Val Trp Phe Val Lys Gly
        35                  40                  45

Asp Leu Leu Arg Pro Gly Phe Leu Ile Ile Met Leu Ala Ser Ala Val
    50                  55                  60

Ser Leu Phe Phe Leu Leu Arg Lys Lys Phe Glu Leu Ala Leu Arg Ile
65                  70                  75                  80

Ile Leu Ile Ala Ser Val Ile Ala Val Ser Val Gly Trp Phe Phe Gly
                85                  90                  95

Leu Ser Gln Gly Asn Ser Pro Leu Asp Glu Gly Asn Lys Asn Ile Val
            100                 105                 110

Leu Ala Ile Phe Ile Met Ile Phe Leu Tyr Phe Ala Asn Val Lys Arg
        115                 120                 125

Thr Leu Leu Ile Ala Val Tyr Cys Phe Val Leu Ile Phe Met Glu Glu
    130                 135                 140

Leu Leu Met Gln Gln Ile His Glu Ser Ile His Met Ala Asp Arg Ile
145                 150                 155                 160

Ala Leu Phe Phe Met Phe Ser Val Ile Ser Ile Ile Ala Val Arg Thr
                165                 170                 175

Leu His Gly Ser Ile Glu Glu Lys Asn Glu Leu Ile Gln Glu Ile His
            180                 185                 190

His Arg Val Arg Asn Asn Leu Gln Val Leu Ser Gly Leu Val Glu Met
        195                 200                 205

His Ser Asp Ser Asp Gln Gly Asn Leu Arg Asn Ile Leu Ser Asp Phe
    210                 215                 220

Gln Asn Arg Ile Leu Ala Ile Ser Glu Val His Asn Tyr Leu Tyr Lys
225                 230                 235                 240

Ser Glu Asn Tyr Phe Asp Ile Asp Phe Ser Glu Val Ile Glu Arg Ile
                245                 250                 255

Ile Ala Asn Leu Ile His Lys Phe Gly Lys Gln Ser Val Lys Ile Glu
            260                 265                 270

Asn Leu Thr Glu Gln Ile Phe Leu Arg Ile Glu Tyr Ala Ile Pro Cys
        275                 280                 285

Ala Met Ile Phe Ser Glu Leu Leu Ser Asn Ser Leu Lys His Ala Phe
    290                 295                 300

Ser Ser Asp Met Gly Lys Ile Val Ile Arg Phe His Lys Glu Gly Asn
305                 310                 315                 320

Lys Tyr Arg Leu Gln Ile Glu Asp Asn Gly Ser Gly Ile Ser Asp Ser
                325                 330                 335
```

-continued

```
Lys Thr Trp Leu Lys Pro Lys Thr Ser Gly Phe Lys Leu Ile Gln Leu
            340                 345                 350

Leu Thr Arg Gln Ile Lys Gly Asp Phe Gln Ile Leu Ser Asp Ser Gly
            355                 360                 365

Ser Ile Ala Val Leu Glu Phe Tyr Thr
    370                 375
```

<210> SEQ ID NO 3
<211> LENGTH: 205
<212> TYPE: PRT
<213> ORGANISM: Leptospira interrogans sv pomona

<400> SEQUENCE: 3

```
Met Phe Asn Phe Ser Gln Tyr Leu Thr Asn Gly Phe Glu Arg Phe Pro
1               5                   10                  15

Leu Ile Glu Lys Ser Lys Ser Lys Ile Lys Lys Ile Ile Phe Val Gly
            20                  25                  30

Arg Ile Thr Pro Asn Lys Lys Gln Asp Asp Leu Ile Arg Leu Ala Phe
            35                  40                  45

Ala Tyr Lys Ser Ile Ile Ser Asp Gln Phe Gln Phe Tyr Leu Ala Gly
    50                  55                  60

Phe Ser Ser Lys Glu Leu Tyr Leu Tyr Arg Glu Glu Leu Glu Arg Met
65                  70                  75                  80

Leu Asp Phe Tyr Asp Leu Arg Lys Asn Val Leu Ile Thr Gly Phe Leu
                85                  90                  95

Ser Asp Leu Glu Leu Asn Ser Leu Tyr Gln Glu Ala Asp Ala Phe Val
            100                 105                 110

Ser Met Ser Glu His Glu Gly Phe Cys Val Pro Leu Ile Glu Ala Met
            115                 120                 125

Ile Tyr Arg Ile Pro Ile Leu Ala Phe Ser Gly Gly Ala Val Ser Glu
    130                 135                 140

Thr Leu Asn Gly Ala Gly Val Leu Phe Lys Glu Lys Asn Phe Pro Asn
145                 150                 155                 160

Leu Ala Ile Leu Leu Asn Lys Ile Leu Thr Asp Val Ser Phe Gln Asn
                165                 170                 175

Gln Ile Leu Thr Gly Gln Asp Leu Arg Leu Asn Glu Phe Lys Lys Thr
            180                 185                 190

Asp Tyr Lys Ser Val Leu Arg Lys Ala Leu Glu Ile Ile
            195                 200                 205
```

<210> SEQ ID NO 4
<211> LENGTH: 283
<212> TYPE: PRT
<213> ORGANISM: Leptospira hardjobovis

<400> SEQUENCE: 4

```
Met Ile Ile Asn His Asn Leu Ser Ala Val Asn Ser His Arg Ser Leu
1               5                   10                  15

Lys Phe Asn Glu Leu Ala Val Asp Lys Thr Met Lys Ala Leu Ser Ser
            20                  25                  30

Gly Met Arg Ile Asn Ser Val Ala Asp Asp Ala Phe Gly Leu Ala Val
            35                  40                  45

Ser Glu Lys Leu Arg Thr Gln Ile Asn Gly Leu Arg Gln Ala Glu Arg
    50                  55                  60

Asn Thr Glu Asp Gly Met Ser Phe Ile Gln Thr Ala Glu Gly Phe Leu
65                  70                  75                  80
```

```
Glu Gln Thr Ser Asn Ile Ile Gln Arg Ile Arg Val Leu Ala Ser Arg
                 85                  90                  95

Pro Arg Met Val Ser Gln Gln Arg Lys Ile Ala Ser Leu Gly Arg Trp
            100                 105                 110

Glu Val Leu Cys Ala Gly Gly Pro Lys Ser His Arg Ile Ala Ser Gln
        115                 120                 125

Ala Glu Phe Ile Ser Ser Ser Phe Leu Gly Ala Ile Arg Lys Arg Phe
    130                 135                 140

Thr Gly Arg Val His Val Val Ser Tyr Gly Ala Glu Arg Lys Ser Ala
145                 150                 155                 160

Arg Glu Ile Leu Gln Arg Pro Glu Cys Phe Glu Ser Pro Glu Ala Cys
                165                 170                 175

Lys Ala Asp Gly Arg Pro Ile Ala Ile Ser Ser Pro Glu Glu Ala Asn
            180                 185                 190

Asp Val Ile Gly Leu Ala Asp Ala Ala Leu Thr Arg Ile Met Lys Gln
        195                 200                 205

Arg Ala Asp Met Gly Ala Tyr Tyr Asn Arg Leu Glu Tyr Thr Ala Lys
    210                 215                 220

Gly Val Met Gly Ala Tyr Glu Asn Met Gln Ala Ser Glu Ser Arg Ile
225                 230                 235                 240

Arg Asp Ala Asp Met Ala Glu Glu Val Val Ser Leu Thr Thr Lys Gln
                245                 250                 255

Ile Leu Val Gln Ser Gly Thr Ala Met Leu Ala Gln Ala Asn Met Lys
            260                 265                 270

Pro Asn Ser Val Leu Lys Leu Leu Gln His Ile
        275                 280

<210> SEQ ID NO 5
<211> LENGTH: 603
<212> TYPE: DNA
<213> ORGANISM: Leptospira interrogans sv pomona

<400> SEQUENCE: 5
atgcgatccg ttcaagaaaa gaacgaattg atacaagaaa ttcatcatag agttagaaat      60
aatcttcagg taatttccgg tttagtggaa atgcatagtg ggtctggtaa agagaatctg     120
caaatcatat tatccgattt tcaaaatcgt atattagcaa tatctgaagt tcataattat     180
ttatataagt ccgaaaatta tttcgaaatc gattttgtcg aggtgatgga taagattatt     240
ctaaatcttt cttatagatt gggaaaacgt tcgatcaaga tagaaactga agctgagtct     300
acttttttaa gaatcgaaaa tgcgattcct tgtgctatga ttttcaacga attgttatcc     360
aattctttaa aacacgcttt tcgttcggaa aaaggaaccg ttcaaatttc gtttcgaaaa     420
aaaggagata atattaccct tcaagtttct gacaatggtt caggaatcaa ggatttaaa      480 atttggtcca aaccgaaaac ggctggtttc actttgatac aaatattaac aaaacagatt     540
aaaggtcgtt ttcaaatttt ctctgaaggc ggttttactg cggttttaga gttcaactca     600
atc                                                                    603

<210> SEQ ID NO 6
<211> LENGTH: 1131
<212> TYPE: DNA
<213> ORGANISM: Leptospira interrogans sv pomona

<400> SEQUENCE: 6 atgaaat

-continued

| | |
|---|---|
| agggcgttcc atcttttcat ttttaatgtg gtgtcgcttt tattgggttt atctgtgaat | 120 |
| ttttatgttt ggtttgtgaa aggtgatcta ttacgtcctg gttttttaat catcatgctt | 180 |
| gcatctgcag tctctctgtt ttttttattg agaaaaaaat ttgaattggc tctcagaatt | 240 |
| attttgatcg caagtgtaat tgctgttagc gttggttggt tttttggact ttctcaggga | 300 |
| aattctcctt tggacgaagg gaataaaaat attgttttag ctatatttat tatgattttc | 360 |
| ttatattttg caaatgtaaa gcgaactctt ctaattgcgg tttactgttt tgttttgatt | 420 |
| tttatggaag agcttttaat gcaacaaatt catgaatcta ttcacatggc tgatcgaatc | 480 |
| gctctatttt tcatgttttc tgtaatttcg attatcgccg taagaactct tcatggatcg | 540 |
| attgaagaaa agaacgaatt gatacaagaa attcatcata gagttagaaa taatcttcag | 600 |
| gttctttccg gtttagtaga aatgcatagt gattctgatc aagggaatct taggaatata | 660 |
| ttatctgatt tcaaaatcg tatattagca atatctgaag ttcataatta tttatataag | 720 |
| tccgaaaatt atttcgacat agattttca gaagtgattg aaagaatcat tgcaaatctc | 780 |
| attcataaat ttggtaaaca atctgtaaaa atagaaaatt taacgaaaca gattttttta | 840 |
| agaatcgaat atgcgattcc ttgtgctatg attttagtg aacttttatc taattcttta | 900 |
| aaacatgcgt tttcttcgga tatggggaaa attgtcattc ggtttcataa agaaggaaat | 960 |
| aagtatcgtc ttcaaattga agataatggt tctggaatat ctgattctaa aacttggttg | 1020 |
| aaaccaaaaa cttctggttt taaattgatt caacttttga ccagacaaat aaaaggtgat | 1080 |
| tttcaaattc tttcggattc tggttccatt gctgtacttg aattttacac t | 1131 |

<210> SEQ ID NO 7
<211> LENGTH: 618
<212> TYPE: DNA
<213> ORGANISM: Leptopsira interrogans sv pomona

<400> SEQUENCE: 7

| | |
|---|---|
| atgtttaatt tttcccaata cctaaccaat ggttttgaac gttttcctaa atcgaaaaa | 60 |
| tcaaaatcta aaattaaaaa aattatttt gtaggtagga tcactcccaa taaaaaacag | 120 |
| gacgatttga tccgccttgc attcgcgtat aagtctataa tttccgatca gtttcagttt | 180 |
| tatctcgcag gttttagttc taaagaatta tatctttatc gggaagaatt agaaggatg | 240 |
| ttggactttt atgatctcag aaaaaacgtt ttgatcacag gttttctctc cgacttagaa | 300 |
| ctaaattccc tttatcaaga agcggatgct ttcgtttcca tgagtgaaca cgaaggtttc | 360 |
| tgtgttcctc tgatcgaagc catgatttat agaattccga tcctcgcttt ttcaggcggc | 420 |
| gcggtttccg aaactttaaa cggagccggt gttctttta agaaaaaaa ttttccgaac | 480 |
| ttggctattt tactcaataa aattttgact gatgtttctt tccaaaatca aattttaaca | 540 |
| ggccaagatc tacgtctgaa cgaatttaaa aaaacggatt ataaatccgt ccttaggaag | 600 |
| gcacttgaaa tcatctct | 618 |

<210> SEQ ID NO 8
<211> LENGTH: 849
<212> TYPE: DNA
<213> ORGANISM: Leptospira hardjobovis

<400> SEQUENCE: 8

| | |
|---|---|
| atgattatca atcacaacct gagcgcggtg aattctcacc gttctctaaa gttcaacgag | 60 |
| cttgctgtgg acaagacgat gaaggctttg tcttccggta tgcggatcaa ttccgtggcg | 120 |
| gacgacgctt tcggactcgc ggtttctgaa aagctaagaa cgcagatcaa cggtctgcgt | 180 |

```
                                                             -continued caggccgaaa gaaacaccga agacgggatg agcttcattc aaactgccga gggtttcctc     240
gaacagacgt cgaacatcat tcagagaatc cgggtgcttg catccagacc tcgaatggtt     300
tctcagcaac gaaagattgc atctttgggc aggtgggaag tattgtgcgc tggtggacca     360
aagtcccacc gaatcgcttc tcaagctgaa tttataagtt caagctttt agggcaatt      420 cgcaaaaggt tcacgggtcg ggtccatgtg gtttcatatg gggccgaacg aaaatcagcg     480
agagagattt tacagcggcc cgaatgcttc gaaagccctg aagcttgtaa agcggacggg     540
agaccgatcg cgatttcttc tccggaagaa gccaacgatg ttatcggttt agcggatgcg     600
gctcttacga ggatcatgaa gcagagagcg gatatggggg cttattacaa taggctcgag     660
tataccgcaa aagggggtgat gggtgcatat gaaaatatgc aagcatcgga atccagaatt     720
cgggacgccg atatggcgga ggaagttgtc tcgctgacca caaaacaaat actcgttcag     780
agtggtacgg caatgttagc gcaggcaaat atgaaaccga attcggttct caagcttctg     840
cagcatatc                                                             849
```

What is claimed is:

1. An isolated protein antigen of *Leptospira interrogans* sv *pomona* comprising the amino acid sequence of SEQ ID NO: 1.

2. A pharmaceutical composition for inducing an immune response to pathogenic *Leptospira interrogans* sv *pomona* in an animal comprising an immunogenically effective amount of the isolated protein antigen of claim 1 and a pharmaceutically acceptable carrier.

* * * * *

UNITED STATES PATENT AND TRADEMARK OFFICE
CERTIFICATE OF CORRECTION

PATENT NO. : 6,482,924 B1
DATED : November 19, 2002
INVENTOR(S) : Eric A. Utt et al.

It is certified that error appears in the above-identified patent and that said Letters Patent is hereby corrected as shown below:

Columns 33 and 34,
Insert SEQ ID NOS: 9 and 10 as set forth in the sequence listed as attached:

Signed and Sealed this

Seventeenth Day of August, 2004

JON W. DUDAS
*Acting Director of the United States Patent and Trademark Office*

SEQUENCE LISTING

```
<110> Pfizer Products Inc.
      Utt, Eric
      Dearwester, Don
      Willy, Michael Stephen

<120>  LEPTOSPIRA VACCINE ANTIGENS FOR THE PREVENTION OF LEPTOSPIROSIS

<130>  3153.00228

<140>  09/461,920
<141>  1999-12-15

<150>  60/113.288
<151>  1998-12-22

<160>  10

<170>  PatentIn version 3.0

<210>  1
<211>  201
<212>  PRT
<213>  Leptospira interrogans as pomona

<400>  1

Met Arg Ser Val Gln Glu Lys Asn Glu Leu Ile Gln Glu Ile His His
1               5                   10                  15

Arg Val Arg Asn Asn Leu Gln Val Ile Ser Gly Leu Val Glu Met His
            20                  25                  30

Ser Gly Ser Gly Lys Glu Asn Leu Gln Ile Ile Leu Ser Asp Phe Gln
        35                  40                  45

Asn Arg Ile Leu Ala Ile Ser Glu Val His Asn Tyr Leu Tyr Lys Ser
    50                  55                  60

Glu Asn Tyr Phe Glu Ile Asp Phe Val Glu Val Met Asp Lys Ile Ile
65                  70                  75                  80

Leu Asn Leu Ser Tyr Arg Leu Gly Lys Arg Ser Ile Lys Ile Glu Thr
                85                  90                  95

Glu Ala Glu Ser Thr Phe Leu Arg Ile Glu Asn Ala Ile Pro Cys Ala
            100                 105                 110

Met Ile Phe Asn Glu Leu Leu Ser Asn Ser Leu Lys His Ala Phe Arg
        115                 120                 125

Ser Glu Leu Gly Thr Val Gln Ile Ser Phe Arg Lys Lys Gly Asp Lys
    130                 135                 140

Tyr Tyr Leu Gln Val Ser Asp Asn Gly Ser Gly Ile Lys Asp Phe Lys
145                 150                 155                 160
```

```
    Ile Trp Ser Lys Pro Lys Thr Ala Gly Phe Thr Leu Ile Gln Ile Leu
                165                 170                 175

Thr Lys Gln Ile Lys Gly Arg Phe Gln Ile Phe Ser Glu Gly Gly Phe
            180                 185                 190

Thr Ala Val Leu Glu Phe Asn Ser Ile
            195                 200

<210>   2
<211>   377
<212>   PRT
<213>   Leptospira interrogans sv pomona

<400>   2

Met Lys Phe Ser Gly Leu Thr Asn His Ile Tyr Lys Asp Arg Asp Tyr
1               5                   10                  15

Leu Thr Arg Asn Arg Ala Phe His Leu Phe Ile Phe Asn Val Val Ser
            20                  25                  30

Leu Leu Leu Gly Leu Ser Val Asn Phe Tyr Val Trp Phe Val Lys Gly
        35                  40                  45

Asp Leu Leu Arg Pro Gly Phe Leu Ile Ile Met Leu Ala Ser Ala Val
    50                  55                  60

Ser Leu Phe Phe Leu Leu Arg Lys Lys Phe Glu Leu Ala Leu Arg Ile
65                  70                  75                  80

Ile Leu Ile Ala Ser Val Ile Ala Val Ser Val Gly Trp Phe Phe Gly
            85                  90                  95

Leu Ser Gln Gly Asn Ser Pro Leu Asp Glu Gly Asn Lys Asn Ile Val
            100                 105                 110

Leu Ala Ile Phe Ile Met Ile Phe Leu Tyr Phe Ala Asn Val Lys Arg
        115                 120                 125

Thr Leu Leu Ile Ala Val Tyr Cys Phe Val Leu Ile Phe Met Glu Glu
    130                 135                 140

Leu Leu Met Gln Gln Ile His Glu Ser Ile His Met Ala Asp Arg Ile
145                 150                 155                 160

Ala Leu Phe Phe Met Phe Ser Val Ile Ser Ile Ile Ala Val Arg Thr
                165                 170                 175

Leu His Gly Ser Ile Glu Glu Lys Asn Glu Leu Ile Gln Glu Ile His
            180                 185                 190

His Arg Val Arg Asn Asn Leu Gln Val Leu Ser Gly Leu Val Glu Met
        195                 200                 205

His Ser Asp Ser Asp Gln Gly Asn Leu Arg Asn Ile Leu Ser Asp Phe
```

```
            210                 215                 220
Gln Asn Arg Ile Leu Ala Ile Ser Glu Val His Asn Tyr Leu Tyr Lys
225             230                 235                 240

Ser Glu Asn Tyr Phe Asp Ile Asp Phe Ser Glu Val Ile Glu Arg Ile
                245                 250                 255

Ile Ala Asn Leu Ile His Lys Phe Gly Lys Gln Ser Val Lys Ile Glu
                260                 265                 270

Asn Leu Thr Glu Gln Ile Phe Leu Arg Ile Glu Tyr Ala Ile Pro Cys
            275                 280                 285

Ala Met Ile Phe Ser Glu Leu Leu Ser Asn Ser Leu Lys His Ala Phe
    290                 295                 300

Ser Ser Asp Met Gly Lys Ile Val Ile Arg Phe His Lys Glu Gly Asn
305                 310                 315                 320

Lys Tyr Arg Leu Gln Ile Glu Asp Asn Gly Ser Gly Ile Ser Asp Ser
                325                 330                 335

Lys Thr Trp Leu Lys Pro Lys Thr Ser Gly Phe Lys Leu Ile Gln Leu
            340                 345                 350

Leu Thr Arg Gln Ile Lys Gly Asp Phe Gln Ile Leu Ser Asp Ser Gly
            355                 360                 365

Ser Ile Ala Val Leu Glu Phe Tyr Thr
    370                 375

<210>  3
<211>  205
<212>  PRT
<213>  Leptospira interrogans sv pomona

<400>  3

Met Phe Asn Phe Ser Gln Tyr Leu Thr Asn Gly Phe Glu Arg Phe Pro
1               5                   10                  15

Leu Ile Glu Lys Ser Lys Ser Lys Ile Lys Lys Ile Ile Phe Val Gly
            20                  25                  30

Arg Ile Thr Pro Asn Lys Lys Gln Asp Asp Leu Ile Arg Leu Ala Phe
        35                  40                  45

Ala Tyr Lys Ser Ile Ile Ser Asp Gln Phe Gln Phe Tyr Leu Ala Gly
    50                  55                  60

Phe Ser Ser Lys Glu Leu Tyr Leu Tyr Arg Glu Glu Leu Glu Arg Met
65                  70                  75                  80

Leu Asp Phe Tyr Asp Leu Arg Lys Asn Val Leu Ile Thr Gly Phe Leu
                85                  90                  95
```

```
Ser Asp Leu Glu Leu Asn Ser Leu Tyr Gln Glu Ala Asp Ala Phe Val
            100                 105                 110

Ser Met Ser Glu His Glu Gly Phe Cys Val Pro Leu Ile Glu Ala Met
        115                 120                 125

Ile Tyr Arg Ile Pro Ile Leu Ala Phe Ser Gly Gly Ala Val Ser Glu
    130                 135                 140

Thr Leu Asn Gly Ala Gly Val Leu Phe Lys Glu Lys Asn Phe Pro Asn
145                 150                 155                 160

Leu Ala Ile Leu Leu Asn Lys Ile Leu Thr Asp Val Ser Phe Gln Asn
            165                 170                 175

Gln Ile Leu Thr Gly Gln Asp Leu Arg Leu Asn Glu Phe Lys Lys Thr
        180                 185                 190

Asp Tyr Lys Ser Val Leu Arg Lys Ala Leu Glu Ile Ile
    195                 200                 205

<210>   4
<211>   283
<212>   PRT
<213>   Leptospira hardjobovis

<400>   4

Met Ile Ile Asn His Asn Leu Ser Ala Val Asn Ser His Arg Ser Leu
1               5                   10                  15

Lys Phe Asn Glu Leu Ala Val Asp Lys Thr Met Lys Ala Leu Ser Ser
            20                  25                  30

Gly Met Arg Ile Asn Ser Val Ala Asp Asp Ala Phe Gly Leu Ala Val
        35                  40                  45

Ser Glu Lys Leu Arg Thr Gln Ile Asn Gly Leu Arg Gln Ala Glu Arg
    50                  55                  60

Asn Thr Glu Asp Gly Met Ser Phe Ile Gln Thr Ala Glu Gly Phe Leu
65                  70                  75                  80

Glu Gln Thr Ser Asn Ile Ile Gln Arg Ile Arg Val Leu Ala Ser Arg
            85                  90                  95

Pro Arg Met Val Ser Gln Gln Arg Lys Ile Ala Ser Leu Gly Arg Trp
        100                 105                 110

Glu Val Leu Cys Ala Gly Gly Pro Lys Ser His Arg Ile Ala Ser Gln
    115                 120                 125

Ala Glu Phe Ile Ser Ser Ser Phe Leu Gly Ala Ile Arg Lys Arg Phe
    130                 135                 140

Thr Gly Arg Val His Val Val Ser Tyr Gly Ala Glu Arg Lys Ser Ala
```

```
            145                 150                 155                 160
    Arg Glu Ile Leu Gln Arg Pro Glu Cys Phe Glu Ser Pro Glu Ala Cys
                    165                 170                 175

Lys Ala Asp Gly Arg Pro Ile Ala Ile Ser Ser Pro Glu Glu Ala Asn
                180                 185                 190

Asp Val Ile Gly Leu Ala Asp Ala Ala Leu Thr Arg Ile Met Lys Gln
            195                 200                 205

Arg Ala Asp Met Gly Ala Tyr Tyr Asn Arg Leu Glu Tyr Thr Ala Lys
        210                 215                 220

Gly Val Met Gly Ala Tyr Glu Asn Met Gln Ala Ser Glu Ser Arg Ile
    225                 230                 235                 240

Arg Asp Ala Asp Met Ala Glu Glu Val Val Ser Leu Thr Thr Lys Gln
                    245                 250                 255

Ile Leu Val Gln Ser Gly Thr Ala Met Leu Ala Gln Ala Asn Met Lys
                260                 265                 270

Pro Asn Ser Val Leu Lys Leu Leu Gln His Ile
            275                 280

<210>   5
<211>   603
<212>   DNA
<213>   Leptospira interrogans sv pomona

<400>   5
atgcgatccg ttcaagaaaa gaacgaattg atacaagaaa ttcatcatag agttagaaat      60
aatcttcagg taatttccgg tttagtggaa atgcatagtg ggtctggtaa agagaatctg     120
caaatcatat tatccgattt tcaaaatcgt atattagcaa tatctgaagt tcataattat     180
ttatataagt ccgaaaatta tttcgaaatc gattttgtcg aggtgatgga taagattatt     240
ctaaatcttt cttatagatt gggaaaacgt tcgatcaaga tagaaactga agctgagtct     300
acttttttaa gaatcgaaaa tgcgattcct tgtgctatga ttttcaacga attgttatcc     360
aattctttaa aacacgcttt tcgttcggaa aaaggaaccg ttcaaatttc gtttcgaaaa     420
aaaggagata aatattacct tcaagtttct gacaatggtt caggaatcaa ggattttaaa     480
atttggtcca aaccgaaaac ggctggtttc actttgatac aaatattaac aaaacagatt     540
aaaggtcgtt ttcaaatttt ctctgaaggc ggttttactg cggttttaga gttcaactca     600
atc                                                                   603

<210>   6
<211>   1131
```

<212> DNA
<213> Leptospira interrogans sv pomona

<400> 6

| | | | | | |
|---|---|---|---|---|---|
| atgaaatttt | caggattaac | caatcatatt | tataaagaca | gggattatct | tactcgaaat | 60 |
| agggcgttcc | atcttttcat | ttttaatgtg | gtgtcgcttt | tattgggttt | atctgtgaat | 120 |
| ttttatgttt | ggtttgtgaa | aggtgatcta | ttacgtcctg | gttttttaat | catcatgctt | 180 |
| gcatctgcag | tctctctgtt | ttttttattg | agaaaaaaat | ttgaattggc | tctcagaatt | 240 |
| attttgatcg | caagtgtaat | tgctgttagc | gttggttggt | ttttggact | ttctcaggga | 300 |
| aattctcctt | tggacgaagg | gaataaaaat | attgttttag | ctatatttat | tatgattttc | 360 |
| ttatattttg | caaatgtaaa | gcgaactctt | ctaattgcgg | tttactgttt | tgttttgatt | 420 |
| tttatggaag | agcttttaat | gcaacaaatt | catgaatcta | ttcacatggc | tgatcgaatc | 480 |
| gctctatttt | tcatgttttc | tgtaatttcg | attatcgccg | taagaactct | tcatggatcg | 540 |
| attgaagaaa | agaacgaatt | gatacaagaa | attcatcata | gagttagaaa | taatcttcag | 600 |
| gttctttccg | gtttagtaga | aatgcatagt | gattctgatc | aagggaatct | taggaatata | 660 |
| ttatctgatt | ttcaaaatcg | tatattagca | atatctgaag | ttcataatta | tttatataag | 720 |
| tccgaaaatt | atttcgacat | agattttca | gaagtgattg | aaagaatcat | tgcaaatctc | 780 |
| attcataaat | ttggtaaaca | atctgtaaaa | atagaaaatt | taacggaaca | gattttttta | 840 |
| agaatcgaat | atgcgattcc | ttgtgctatg | attttagtg | aacttttatc | taattcttta | 900 |
| aaacatgcgt | tttcttcgga | tatggggaaa | attgtcattc | ggtttcataa | agaaggaaat | 960 |
| aagtatcgtc | ttcaaattga | agataatggt | tctggaatat | ctgattctaa | aacttggttg | 1020 |
| aaaccaaaaa | cttctggttt | taaattgatt | caacttttga | ccagacaaat | aaaaggtgat | 1080 |
| tttcaaattc | tttcggattc | tggttccatt | gctgtacttg | aattttacac | t | 1131 |

<210> 7
<211> 618
<212> DNA
<213> Leptopsira interrogans sv pomona

<400> 7

| | | | | | |
|---|---|---|---|---|---|
| atgtttaatt | tttcccaata | cctaaccaat | ggttttgaac | gttttcctaa | aatcgaaaaa | 60 |
| tcaaaatcta | aaattaaaaa | aattattttt | gtaggtagga | tcactcccaa | taaaaaacag | 120 |
| gacgatttga | tccgccttgc | attcgcgtat | aagtctataa | tttccgatca | gtttcagttt | 180 |
| tatctcgcag | gttttagttc | taaagaatta | tatctttatc | gggaagaatt | agaaaggatg | 240 |

```
ttggactttt atgatctcag aaaaaacgtt ttgatcacag gttttctctc cgacttagaa    300
ctaaattccc tttatcaaga agcggatgct ttcgtttcca tgagtgaaca cgaaggtttc    360
tgtgttcctc tgatcgaagc catgatttat agaattccga tcctcgcttt ttcaggcggc    420
gcggtttccg aaactttaaa cggagccggt gttcttttta agaaaaaaaa ttttccgaac    480
ttggctattt tactcaataa aattttgact gatgtttctt tccaaaatca aattttaaca    540
ggccaagatc tacgtctgaa cgaatttaaa aaaacggatt ataaatccgt ccttaggaag    600
gcacttgaaa tcatctct                                                  618

<210>   8
<211>   849
<212>   DNA
<213>   Leptospira hardjobovis

<400>   8
atgattatca atcacaacct gagcgcggtg aattctcacc gttctctaaa gttcaacgag     60
cttgctgtgg acaagacgat gaaggctttg tcttccggta tgcggatcaa ttccgtggcg    120
gacgacgctt tcggactcgc ggtttctgaa aagctaagaa cgcagatcaa cggtctgcgt    180
caggccgaaa gaaacaccga agacgggatg agcttcattc aaactgccga gggtttcctc    240
gaacagacgt cgaacatcat tcagagaatc cgggtgcttg catccagacc tcgaatggtt    300
tctcagcaac gaaagattgc atctttgggc aggtgggaag tattgtgcgc tggtggacca    360
aagtcccacc gaatcgcttc tcaagctgaa tttataagtt caagcttttt agggcaatt     420
cgcaaaaggt tcacgggtcg ggtccatgtg gtttcatatg gggccgaacg aaaatcagcg    480
agagagattt tacagcggcc cgaatgcttc gaaagccctg aagcttgtaa agcggacggg    540
agaccgatcg cgatttcttc tccggaagaa gccaacgatg ttatcggttt agcggatgcg    600
gctcttacga ggatcatgaa gcagagagcg gatatggggg cttattacaa taggctcgag    660
tataccgcaa aagggggtgat gggtgcatat gaaaatatgc aagcatcgga atccagaatt    720
cgggacgccg atatggcgga ggaagttgtc tcgctgacca caaaacaaat actcgttcag    780
agtggtacgg caatgttagc gcaggcaaat atgaaaccga attcggttct caagcttctg    840
cagcatatc                                                            849
```

<210> 9
<211> 26
<212> DNA
<213> AUS1 PRIMER

<400> 9
gatcggacgg tgaattctcg agagtg                                    26

<210> 10
<211> 24
<212> DNA
<213> AUS2 PRIMER

<400> 10
gacactctcg agaattcacc gtcc                                      24